(12) United States Patent
Mosebach et al.

(10) Patent No.: US 10,918,811 B2
(45) Date of Patent: Feb. 16, 2021

(54) AUDIBLE INDICATOR

(71) Applicant: SANOFI-AVENTIS DEUTSCHLAND GMBH, Frankfurt am Main (DE)

(72) Inventors: Carsten Mosebach, Frankfurt am Main (DE); Thomas Mark Kemp, Ashwell (GB); Louise Hodgson, Herts (GB); William Timmis, Melbourn (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 257 days.

(21) Appl. No.: 15/578,491

(22) PCT Filed: Jun. 2, 2016

(86) PCT No.: PCT/EP2016/062454
§ 371 (c)(1),
(2) Date: Nov. 30, 2017

(87) PCT Pub. No.: WO2016/193348
PCT Pub. Date: Dec. 8, 2016

(65) Prior Publication Data
US 2018/0154089 A1    Jun. 7, 2018

(30) Foreign Application Priority Data
Jun. 3, 2015 (EP) .................................... 15170588

(51) Int. Cl.
*A61M 5/50*    (2006.01)
*A61M 5/20*    (2006.01)
(Continued)

(52) U.S. Cl.
CPC ........ *A61M 5/5086* (2013.01); *A61M 5/2033* (2013.01); *A61M 5/24* (2013.01);
(Continued)

(58) Field of Classification Search
CPC .... A61M 5/24; A61M 5/2448; A61M 5/2033; A61M 5/3202; A61M 5/3157;
(Continued)

(56) References Cited

U.S. PATENT DOCUMENTS

| 4,629,454 A | 12/1986 | Grier |
| 4,810,249 A | 3/1989 | Haber et al. |

(Continued)

FOREIGN PATENT DOCUMENTS

| CN | 101107032 | 1/2008 |
| CN | 201243374 | 5/2009 |

(Continued)

OTHER PUBLICATIONS

International Search Report and Written Opinion in International Application No. PCT/EP2016/062454, dated Aug. 5, 2016, 9 pages.

(Continued)

*Primary Examiner* — Tiffany Legette
(74) *Attorney, Agent, or Firm* — Fish & Richardson P.C.

(57) ABSTRACT

The disclosure relates to an audible indicator in combination with a drug delivery device having a resilient force member capable of resting in either of two states. In a biased state, the resilient force member is biased and stores energy and in a relaxed state, the resilient force member is relaxed. The resilient force member releases the stored energy when changing from the biased state into the relaxed state, thereby generating an audible signal, wherein the resilient force member is supported by a retaining element in the biased state in order to prevent transition into the relaxed state.

17 Claims, 21 Drawing Sheets

(51) Int. Cl.
*A61M 5/24* (2006.01)
*A61M 5/32* (2006.01)

(52) U.S. Cl.
CPC ........ *A61M 5/2448* (2013.01); *A61M 5/3202* (2013.01); *A61M 2205/43* (2013.01); *A61M 2205/581* (2013.01)

(58) Field of Classification Search
CPC ............ A61M 5/5086; A61M 2205/43; A61M 2205/581; A61M 5/31578; A61M 2005/202
See application file for complete search history.

(56) References Cited

U.S. PATENT DOCUMENTS

| | | | |
|---|---|---|---|
| 5,114,406 | A | 5/1992 | Gabriel et al. |
| 5,116,313 | A | 5/1992 | McGregor |
| 5,127,906 | A | 7/1992 | Landry et al. |
| 5,271,527 | A | 12/1993 | Haber et al. |
| 7,611,495 | B1 | 11/2009 | Gianturco |
| 9,168,339 | B2 | 10/2015 | Cowe |
| 9,199,038 | B2 | 12/2015 | Daniel |
| 9,216,251 | B2 | 12/2015 | Daniel |
| 9,744,306 | B2 | 8/2017 | Cowe |
| 9,764,096 | B2 | 9/2017 | Maritan |
| 2004/0210199 | A1 | 10/2004 | Atterbury et al. |
| 2007/0088248 | A1 | 4/2007 | Glenn et al. |
| 2008/0021373 | A1 | 1/2008 | Rosati |
| 2010/0198182 | A1 | 8/2010 | Lanigan et al. |
| 2011/0026721 | A1* | 2/2011 | Parker .................... H04R 25/70 381/59 |
| 2011/0105952 | A1 | 5/2011 | Bernstein et al. |
| 2013/0090605 | A1 | 4/2013 | O'Connor et al. |
| 2013/0906605 | | 4/2013 | O'Connor et al. |
| 2013/0345642 | A1* | 12/2013 | Cowe ..................... A61M 5/20 604/189 |
| 2014/0243751 | A1 | 8/2014 | Brereton et al. |
| 2014/0276568 | A1 | 9/2014 | Worden et al. |
| 2016/0008541 | A1 | 1/2016 | Hirschel et al. |
| 2016/0144133 | A1 | 5/2016 | Kemp |

FOREIGN PATENT DOCUMENTS

| | | |
|---|---|---|
| CN | 104080499 | 10/2014 |
| CN | 104519929 | 4/2015 |
| DE | 7833454 | 5/1979 |
| DE | 3935672 | 11/1990 |
| EP | 2727617 | 5/2014 |
| EP | 2868338 | 5/2015 |
| JP | H07-509636 | 10/1995 |
| JP | 2012-504006 | 2/2012 |
| JP | 2013-526904 | 6/2013 |
| JP | 2013-534164 | 9/2013 |
| JP | H5-508098 | 5/2014 |
| RU | 2140794 | 11/1999 |
| RU | 2012137269 | 3/2014 |
| WO | WO 92/17223 | 10/1992 |
| WO | WO 94/03222 | 2/1994 |
| WO | WO 02/092153 | 11/2002 |
| WO | WO 2005/046773 | 5/2005 |
| WO | WO 2006/079481 | 8/2006 |
| WO | WO 2010/035057 | 4/2010 |
| WO | WO 2011/079278 | 6/2011 |
| WO | WO 2011/123024 | 10/2011 |
| WO | WO 2012/022810 | 2/2012 |
| WO | WO 2013/057033 | 4/2013 |
| WO | WO 2013/057034 | 4/2013 |
| WO | WO 2014/005808 | 1/2014 |
| WO | WO 2014/139914 | 9/2014 |
| WO | WO 2014/139922 | 9/2014 |
| WO | WO 2014/164943 | 10/2014 |
| WO | WO 2015/004050 | 1/2015 |
| WO | WO 2015/062915 | 5/2015 |
| WO | WO 2016/193343 | 12/2016 |
| WO | WO 2016/193344 | 12/2016 |

OTHER PUBLICATIONS

International Preliminary Report on Patentability in International Application No. PCT/EP2016/062454, dated Dec. 5, 2017, 7 pages.
Karpova, "The basics of surdopedagogy", Ekaterinburg, pp. 20-21, 2008.
PCT International Preliminary Report on Patentability in International Appln. No. PCT/EP2016/062449, dated Dec. 5, 2017, 6 pages.
PCT International Preliminary Report on Patentability in International Appln. No. PCT/EP2016/062452, dated Dec. 5, 2017, 7 pages.
PCT International Preliminary Report on Patentability in International Appln. No. PCT/EP2018/079917, dated May 5, 2020, 8 pages.
PCT International Search Report and Written Opinion in International Appln. No. PCT/EP2016/062449, dated Aug. 17, 2016, 8 pages.
PCT International Search Report and Written Opinion in International Appln. No. PCT/EP2016/062452, dated Sep. 15, 2016, 11 pages.
PCT International Search Report and Written Opinion in International Appln. No. PCT/EP2018/079915, dated Dec. 5, 2018, 13 pages.
PCT International Search Report and Written Opinion in International Appln. No. PCT/EP2018/079917, dated Dec. 5, 2018, 10 pages.

\* cited by examiner

AUDIBLE INDICATOR

CROSS REFERENCE TO RELATED APPLICATIONS

The present application is the national stage entry of International Patent Application No. PCT/EP2016/062454, filed on Jun. 2, 2016, and claims priority to Application No. EP 15170588.6, filed in on Jun. 3, 2015, the disclosures of which are expressly incorporated herein in entirety by reference thereto.

TECHNICAL FIELD

The disclosure relates to an audible indicator.

BACKGROUND

Administering an injection is a process which presents a number of risks and challenges for users and healthcare professionals, both mental and physical. Injection devices typically fall into two categories—manual devices and auto-injectors. In a conventional manual device, manual force is required to drive a medicament through a needle. This is typically done by some form of button/plunger that has to be continuously pressed during the injection. There are numerous disadvantages associated with this approach. For example, if the button/plunger is released prematurely, the injection will stop and may not deliver an intended dose. Furthermore, the force required to push the button/plunger may be too high (e.g., if the user is elderly or a child). And, aligning the injection device, administering the injection, and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and a trigger button or other mechanism may be used to activate the injection. Autoinjectors may be single-use or reusable devices.

Furthermore, it is necessary to administer the full dose in order to achieve full effectiveness of the medicament within the patient.

Thus, there remains a need for an audible indicator for a drug delivery device. Current indicators may be too quiet or too bulky to use in current autoinjectors and other drug delivery devices. The audible indicators described herein solve one or more of these problems.

SUMMARY

According to aspects of the current disclosure, there is provided an audible indicator for use with a drug delivery device, the audible indicator comprising a monostable resilient force member configured to reside in either of two states having two different conformations. In a relaxed state, the resilient force member is relaxed in a first conformation. In a biased state, the resilient force member is biased to store energy in a second conformation different to the first conformation. The resilient force member releases stored energy to generate an audible signal when changing from the biased state into the relaxed state due to a transition from the second conformation to the first conformation, wherein the resilient force member is supported by a retaining element in the biased state in order to prevent transition into the relaxed state.

As opposed to a bistable spring element, which has to stable states, a monostable spring element may have only one stable state. If resiliently deformed from out of this stable state and subsequently released, the monostable spring element will return to this stable state. In order to keep a monostable spring element in an instable state, an additional component supporting the monostable spring element in the instable state is required.

The audible indicator can be used for indicating to a patient or user that the full dose of medicament in the drug delivery device was spent. Thus, the drug delivery device is improved in order to achieve a reliable indication of the end of medicament delivery and a full effectiveness of the medicament within the patient.

In an exemplary embodiment, the retaining element is a plunger, wherein the resilient force member is allowed to transition from the biased state by a movement of the plunger that is used to displace the drug from a medicament container.

In another exemplary embodiment, the retaining element is adapted to be moved or allowed to move by a plunger or by a drive spring, wherein this movement of the retaining element allows transition of the resilient force member from the biased state.

For example, the resilient force member may be allowed to transition from the biased state into the relaxed state when the plunger moves towards or reaches a proximal position at the end of a medicament delivery process.

In an exemplary embodiment, the resilient force member includes a leaf spring having a longitudinal axis, wherein the resilient force member is bent by a certain angle about the longitudinal axis forming two angled wing-shaped sections. This enables a priming of the audible indicator with little effort.

In an exemplary embodiment, the leaf spring has a rectangular shape, a square shape or an oval shape It is understood that a monostable leaf spring can store energy in the form of tension on one or more outer edges of one or more wing-shaped sections. It is also understood that the monostable leaf spring can also store energy in the form of compression in a central region of one or more wing-shaped sections.

For example, the resilient force member is supported when the drug delivery device is in an initial state. Alternatively, the resilient force member is supported when the drug delivery device is in an initial state and in a primed state, wherein a proximal spring section of the resilient force member is supported by a supporting protrusion arranged on a rear case.

The resilient force member is configured as a monostable spring element. As opposed to a bistable spring element, a monostable spring element may have only one stable state. In order to keep a monostable spring element in an instable state, an additional component supporting the monostable spring element in the instable state is required. For example, the retaining element is a flexible arm arranged on a rear case and the resilient force member rests in the biased state by support of the flexible arm. In an exemplary embodiment, the flexible arm may be biased by an outer circumference of a plunger. Thus, the resilient force member may change from the biased state into the relaxed state when the flexible arm releases. Alternatively, the retaining element is a cantilever beam arranged on a rear case, wherein the resilient force member rests in the biased state by support of the cantilever beam. In an exemplary embodiment, the cantilever beam is biased by an outer circumference of a plunger. Hence, the resilient force member may transition from the biased state into the relaxed state when the cantilever beam releases.

In an exemplary embodiment, the audible indicator is capable of producing an audible signal with a volume of at least 100 dB.

In an exemplary embodiment, the resilient force member is bent about a longitudinal bend such that the two-wing-shaped sections are at an angle of between 130 degrees and 160 degrees relative to each other. For example, the angle can be between 130 degrees and 140 degrees or between 140 degrees and 155 degrees or between 132 degrees and 142 degrees or between 134 degrees and 140 degrees or between 136 degrees and 138 degrees. In an exemplary embodiment, the angle is approximately or exactly 136 degrees or 137 degrees or 138 degrees or 148 degrees or 152 degrees.

The audible indicator may be part of a drug delivery device.

In some embodiments, a method of assembling a drug delivery device can comprise the steps of bending a resilient force member about a longitudinal axis extending generally from a first end of the resilient force member to a second end of the resilient force member located generally opposite the first end. For example, the first end may be a distal end and the second send may be a proximal end of the resilient force member. In some embodiments, the resilient force member can be bent about the longitudinal axis or bend such that the two-wing-shaped sections are at an angle of between about 130 degrees and about 160 degrees relative to each other. For example, the angle can be between 130 degrees and 140 degrees or between 140 degrees and 155 degrees or between 132 degrees and 142 degrees or between 134 degrees and 140 degrees or between 136 degrees and 138 degrees. In an exemplary embodiment, the angle is approximately or exactly 136 degrees or 137 degrees or 138 degrees or 148 degrees or 152 degrees.

Such bending may plastically deform the resilient force member to form two wing-shaped sections angled relative to each other about the longitudinal axis. It is contemplated that the two sections may have approximately the same shape or size. With such bending, the resilient force member may assume a first conformation.

The assembly method can also include flexing the resilient force member about an axis (A) running substantially perpendicular to the longitudinal axis or bend described above. Such flexing may elastically deform the resilient force member, converting its state from a relaxed state (S1) to a biased state (S2). In the biased state, the resilient force member can assume a second conformation different to the first conformation.

As described herein, the biased state can be unsupported (e.g., bistable), where no additional forces are applied to the resilient force member to maintain the second conformation. The biased state can also be maintained with support (e.g., monostable), where one or more additional or retaining forces are applied to the resilient force member to maintain the second conformation. Converting a bistable member from S2 to S1 can require application of an additional force to the resilient force member, while converting a monostable member from S2 to S1 can require at least partial removal of a retaining force from the resilient force member. Conversion from S2 to S1 can cause the resilient force member to generate a surprisingly loud sound signal.

The method can further include coupling the resilient force member of the drug delivery device. For example, the resilient force member can be fixedly coupled or movingly coupled to one or more parts of the drug delivery device. Fixed coupling can include co-molding, adhesive or chemical bonding, screws, etc. Moveable coupling can include locating at least part of the resilient force member within a complementary recess, or providing the resilient force member with one or more complementary recesses. For example, the resilient force member can include one or more protrusions designed to fit generally within one or more complementary recesses of a syringe carriers. The one or more protrusions can be located at various positions on the resilient force member. The resilient force member can also include one or more complementary recesses or a combination of protrusion or recess. Such an arrangement of one or more protrusions and recesses can facilitate efficient component transport, priming of the resilient force member, component assembly, or assembly of the device.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given herein below and the accompanying drawings which are given by way of illustration only, and thus, are not limitative of the present disclosure, and wherein.

Corresponding parts are marked with the same reference symbols in all figures.

DETAILED DESCRIPTION

In the present application, when the term "distal section/end" is used, this refers to the section/end of the device, or the sections/ends of the components thereof, which during use of the device is located closest to a medicament delivery site of a patient. Correspondingly, when the term "proximal section/end" is used, this refers to the section/end of the device, or the sections/ends of the components thereof, which during use of the device is pointing away from the medicament delivery site of the patient.

FIGS. 1 to 6 respectively show a first embodiment of an audible indicator 13 of an exemplary embodiment of a drug delivery device 1 which will be described further below.

Figure 1:
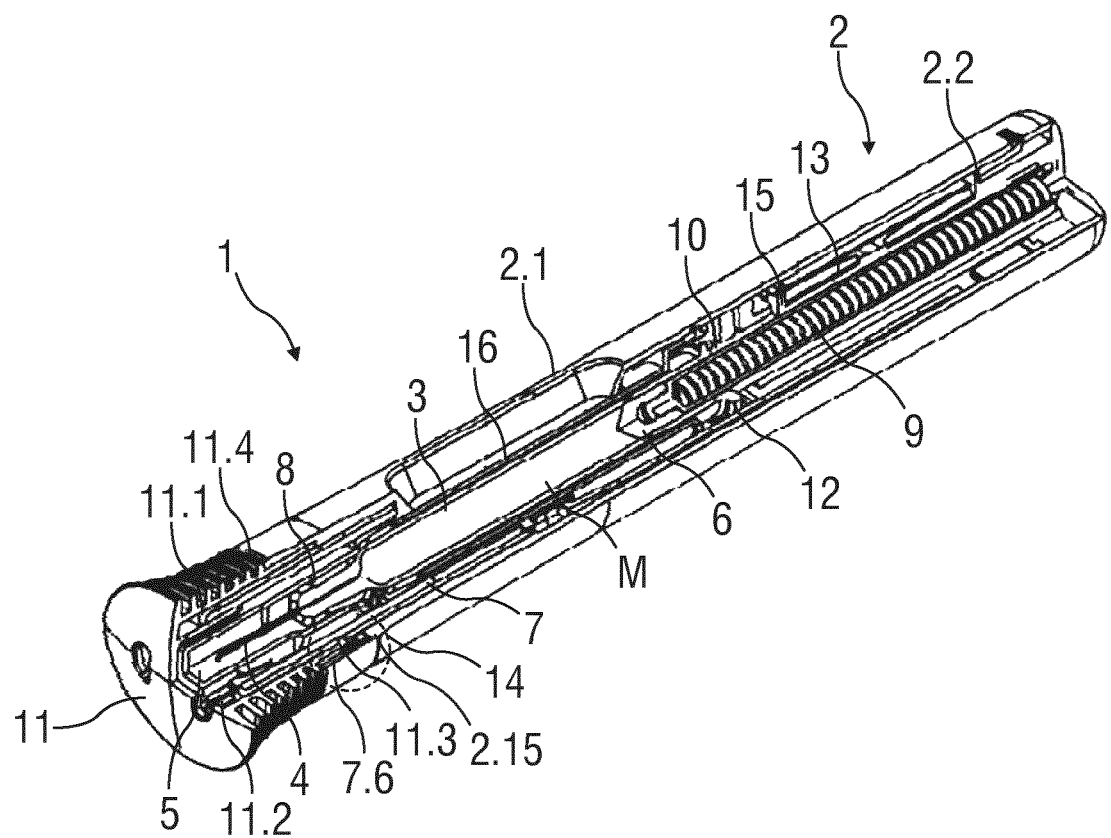
FIG. 1 is a schematic perspective partial section of a drug delivery device comprising an audible indicator according to a first embodiment.

FIG. 1 is a schematic perspective partial section of an exemplary embodiment of the drug delivery device 1 configured as an autoinjector.

In the shown exemplary embodiment, the drug delivery device 1 comprises a case 2 with a front case 2.1 and a rear case 2.2. The case 2 is adapted to hold a medicament container 3, such as a syringe. (The medicament container is referred to hereinafter as the "syringe 3"). The syringe 3 may be a pre-filled syringe, in particular a 1.0 ml pre-filled syringe, containing a medicament M and having a needle 4 arranged at a distal end of the syringe 3. In another exemplary embodiment, the medicament container 3 may be a cartridge which includes the medicament M and engages a removable needle (e.g., by threads, snaps, friction, etc.).

The drug delivery device 1 further comprises a protective needle sheath 5 that is coupled to the needle 4. For example, the protective needle sheath 5 is removably coupled to the needle 4. The protective needle sheath 5 may be a rubber needle sheath or a rigid needle sheath which is composed of rubber and a full or partial plastic shell.

For sealing the syringe 3 proximally and for displacing a medicament M contained in the syringe 3 through the needle 4, a stopper 6 is provided and arranged within the syringe 3.

In the shown exemplary embodiment, the drug delivery device 1 comprises a needle shroud 7 that is telescopically coupled to the case 2 and movable between a first extended position relative to the case 2 in which the needle 4 is covered and a retracted position relative to the case 2 in which the needle 4 is exposed. Furthermore, a shroud spring 8 is arranged to bias the needle shroud 7 distally against the case 2.

Furthermore, a drive spring 9 is arranged within the case 2. Furthermore, a plunger 10 serves for forwarding a force of the drive spring 9 to the stopper 6. The plunger 10 may be hollow, wherein the drive spring 9 is arranged within the plunger 10 biasing the plunger 10 distally against the case 2. In another exemplary embodiment, the plunger 10 may be solid and the drive 9 may engage a proximal end of the plunger 10. In the shown exemplary embodiment, the drive spring 9 is wrapped around an outer diameter of the plunger 10 and extends within the syringe 3. The plunger 10 may comprise a proximal plunger section 10.1 and a distal plunger section 10.2 that are configured with different diameters, wherein the diameter of the proximal plunger section 10.1 is larger than the diameter of the distal plunger section 10.2 (not shown in detail in FIGS. 1, 4 and 6).

Additionally, the drug delivery device 1 comprises a cap 11 that may be removably disposed at a distal end of the case 2, in particular at a distal end of the front case 2.1. The cap 11 may comprise grip features 11.1 for facilitating a removal of the cap 11, e.g., by twisting and/or pulling the cap 11 off the case 2. The cap 11 may further include a grip element 11.2, e.g., a barb, a hook, a narrowed section, etc., arranged to engage the protective needle sheath 5, the case 2 and/or the needle shroud 7.

In the shown exemplary embodiment, a plunger release mechanism 12 is arranged for preventing release of the plunger 10 prior to retraction of the needle shroud 7 relative to the case 2 and for releasing the plunger 10 once the needle shroud 7 is sufficiently retracted.

Furthermore, a shroud lock mechanism 14 is arranged to prevent retraction of the needle shroud 7 relative to the case 2 when the cap 11 is in place, thereby avoiding unintentional activation of the drug delivery device 1, e.g., if dropped, during shipping or packaging, etc. The shroud lock mechanism 14 may comprise one or more compliant beams 11.3 on the cap 11 and a respective number of apertures 7.6 in the needle shroud 7 adapted to receive each of the compliant beams 11.3.

When the cap 11 is attached to the drug delivery device 1, the compliant beams 11.3 abut a radial stop 2.15 on the case 2 which prevents the compliant beams 11.3 from disengaging the apertures 7.6. Furthermore, when the cap 11 is attached to the drug delivery device 1, an axial proximal movement of the cap 11 relative to the case 2 is limited by a rib 11.4 on the cap 11 that abuts the case 2.

When the cap 11 is pulled off the case 2 distally, the compliant beams 11.3 may abut an edge of the aperture 7.6 and deflect to disengage the aperture 7.6, allowing for removal of the cap 11 and the protective needle sheath 5 attached thereto. In an exemplary embodiment, the compliant beams 11.3 and/or the apertures 7.6 may be ramped to reduce force necessary to disengage the compliant beams 11.3 from the apertures 7.6.

The drug delivery device 1 further comprises the audible indicator 13 according to the first embodiment for producing an audible feedback for a user or patient indicating completion of medicament delivery. In other words: The audible indicator 13 is provided to indicate to a user or a patient that the full dose of medicament M was spent.

In the following FIGS. 2 to 6, the audible indicator 13 according to the first embodiment will be explained in more detail.

Figure 2:
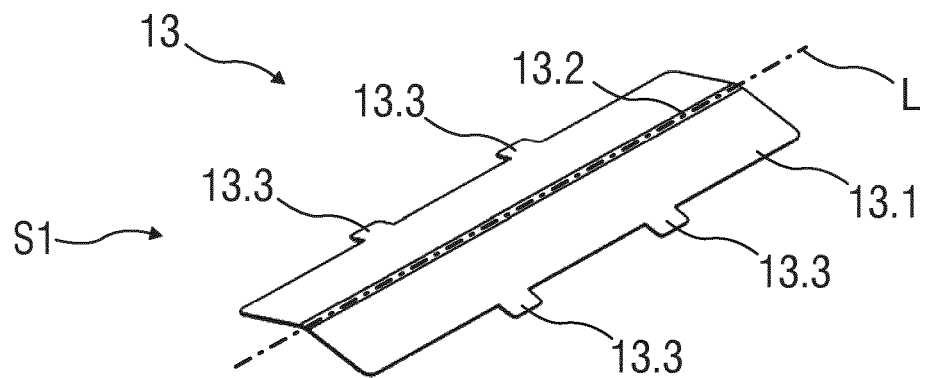
FIG. 2 is a schematic perspective view of the audible indicator according to the first embodiment in a pre-assembled state.
Figure 3:
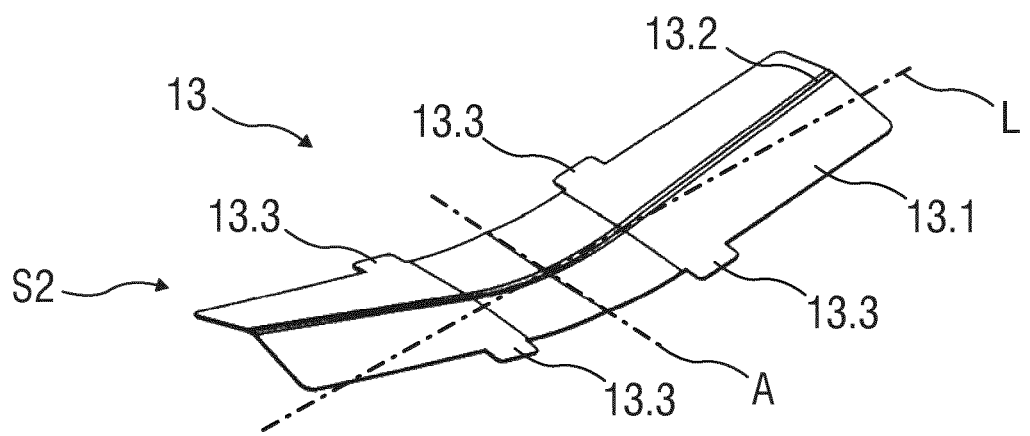
FIG. 3 is a schematic perspective view of the audible indicator according to the first embodiment in a primed state.

FIGS. 2 and 3 are schematic perspective views of the audible indicator 13 according to the first embodiment, wherein FIG. 2 shows the audible indicator 13 in a pre-assembly state and FIG. 3 in a primed state.

The audible indicator 13 comprises a resilient force member 13.1, e.g. having a substantially rectangular shape, comprising a longitudinal axis L running in parallel to the longest side of the outer circumference of the resilient force member 13.1. In other embodiments, the resilient force member 13.1 may have a triangular shape or any other geometrical shape suitable to couple the audible indicator 13 to the autoinjector 1.

The resilient force member 13.1 may be designed as a monostable leaf spring comprising a resilient material, e.g. spring steel or spring plastic. Thus, the resilient force member 13.1 is capable of residing in two states. That is, the resilient force member 13.1 may assume two different conformations, one of them stable with limited or no application of an external force and the other one unstable. For example, these two states can include a first or relaxed state S1 (or pre-assembly state, or trigged state), in which the resilient force member 13.1 has a first conformation. In a second or biased state S2 (or primed state), the resilient force member 13.1 can have a second conformation. In FIG. 2, the resilient force member 13.1 is in the relaxed state S1 which can correspond to the pre-assembly state as well as to a state at the end of medicament delivery.

Regarding the first embodiment, the resilient force member 13.1 comprises a longitudinal bend 13.2. The longitudinal bend 13.2 can be arranged generally in the centre of the resilient force member 13.1 running in parallel to the longitudinal axis L. The longitudinal bend 13.2 can divide the audible indicator 13 into two wing-shaped sections angled to each other with an angle less than 180. In the illustrated perspective of FIG. 2, the wing-shaped sections are angled downwards.

Furthermore, the resilient force member 13.1 can comprise one or more tabs 13.3 projecting radially from the outer circumference. Specifically, the resilient force member 13.1 can include one, two, three four or more tabs 13.3. As shown in FIGS. 2 and 3, the resilient force member 13.1 includes four tabs 13.3, wherein one pair of tabs 13.3 is arranged opposite another pair of tabs 13.3. In another embodiment (not shown), the resilient force member 13.1 can include two tabs 13.3 located generally opposite each other. The pairs of tabs 13.3 are arranged spaced to each other in the direction of the longitudinal axis L. In another exemplary embodiment, the number and arrangement of the tabs 13.3 may differ from the shown exemplary embodiment. In an exemplary embodiment, the tabs 13.3 may be angled with respect to the wing-shaped sections to facilitate assembly of the drug delivery device 1.

The audible indicator 13 is coupled to the case 2 as shown in FIG. 1. In detail, the resilient force member 13.1 is held in the rear case 2.2 such that the longitudinal axis L is in parallel with a longitudinal extension of the drug delivery device 1. The audible indicator 13 is coupled to the drug delivery device 1 by a snap connection, wherein one or more of the tabs 13.3 are engaged within a number of corresponding openings (not shown) in the rear case 2.2. In another exemplary embodiment, the resilient force member 13.1 is held in the rear case 2.2 by a frictional connection, such as a screw or rivet connection or interference fit.

For assembling the audible indicator 13 into the drug delivery device 1, the resilient force member 13.1 is bent in the center about an axis A running perpendicular to the longitudinal axis L. The bending angle is less than 90 degrees. This bending is achieved by applying a predetermined force onto or near the center point of the resilient force member 13.1 when engaging the tabs 13.3 within the openings in the rear case 2.2. As a result, the resilient force member 13.1 changes from the relaxed state S1 into the biased state S2. Two ends 13.1.1, 13.1.2 of the resilient force member 13.1 at opposite ends along the longitudinal axis L are angled upwards from the center point in the illustrated perspective of FIG. 3, which shows the biased state S2. Hence, the biased state S2 corresponds with the primed state, wherein the resilient force member 13.1 stores a certain amount of energy.

Figure 4:
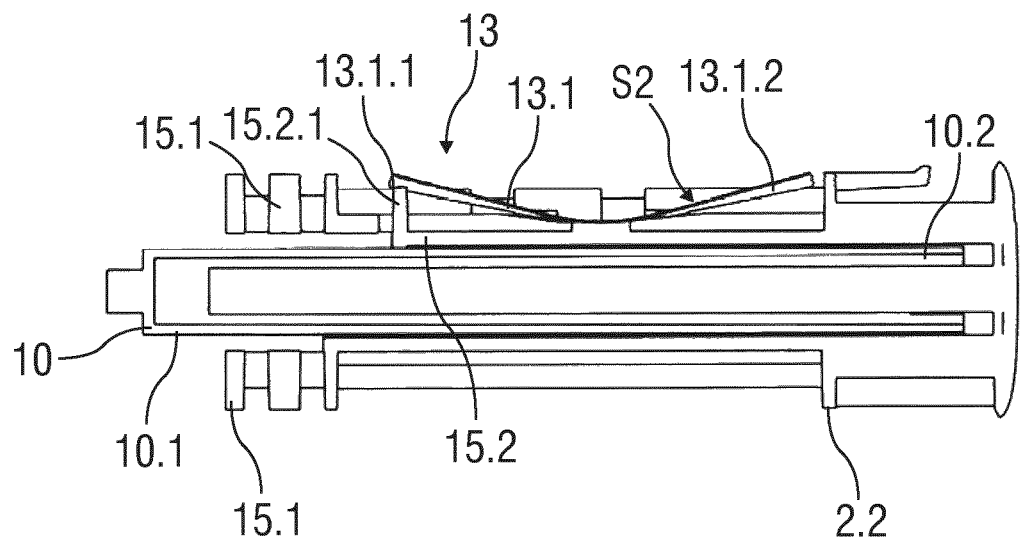
FIG. 4 is a schematic longitudinal section of a drive sub assembly of the drug delivery device comprising a rear case, a plunger and the audible indicator according to the first embodiment in the primed state.

After removing the applied force, the resilient force member 13.1 is held in the biased state S2 as it is shown in FIG. 4 and described below.

FIG. 4 shows a longitudinal section of an exemplary embodiment of a drive subassembly 1.1 of the drug delivery device 1.

The drive sub assembly 1.1 is a sub assembly of the drug delivery device 1 and comprises the components required to deliver the medicament M. The drive subassembly 1.1 comprises the rear case 2.2, the plunger 10 and the audible indicator 13 according to the first embodiment. The drug delivery device 1 further comprises a front sub assembly (not shown separately) to allow for flexibility as to the time and location of manufacture of the subassemblies and final assembly with the syringe 3.

According to the present embodiment, the rear case 2.2 comprises two support arms 15.1 adapted to support an axial position of the syringe 3 during storage, transportation and medicament delivery. The support arms 15.1 project distally from a distal end of the rear case 2.2. The rear case 2.2 further comprises an additional flexible arm 15.2 that projects distally from the distal end of the rear case 2.2 as well. The flexible arm 15.2 is adapted to damp impact forces and thus to stabilize the resilient force member 13.1 in its biased state S2 during storage, transportation, and medicament delivery.

The resilient force member 13.1 is in the biased state S2 and held in the rear case 2.2 by the snap connection as described above. The distally pointing end 13.1.1 of the resilient force member 13.1 is supported by a projection 15.2.1 of the flexible arm 15.2 arranged on a distal end of the flexible arm 15.2. The proximally pointing end 13.1.2 of the resilient force member 13.1 is free and not in contact with any other component and located above the flexible arm 15.2 or another section of the rear case 2.2. In an exemplary embodiment, the rear case 2.2 may comprise a plurality of flexible arms 15.2 that are arranged around a circumference of the proximal end of the rear case 2.2.

Furthermore, the flexible arm 15.2 is deflected outwards supported by the outer circumference of the plunger 10 as is shown in FIG. 4.

Figure 5:
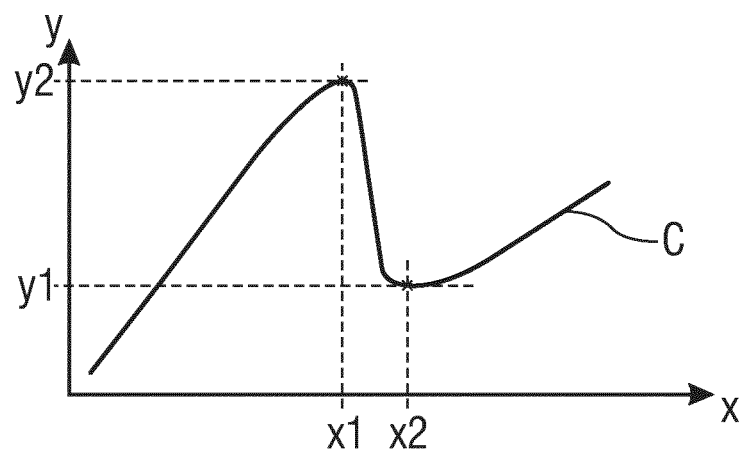
FIG. 5 is a diagram with a force-bending curve of the audible indicator according to the first embodiment.

After changing from the relaxed state S1 into the biased state S2 as described before, only a small force may be required to hold the resilient force member 13.1 in the biased state S2. This is achieved by the longitudinal bend 13.2 that provides a bended cross section of the resilient force member 13.1 which buckles into a new configuration by changing from the relaxed state S1 into the biased state S2. In this configuration, a stiffness of the material structure is significantly reduced and thus only a small holding force is required to maintain the resilient force member 13.1 in the biased state S2. FIG. 5 shows a diagram with a force-bending curve C of the resilient force member 13.1.

The diagram comprises an abscissa x and an ordinate y. The abscissa x represents the bending deflection and the ordinate y represents the force required for achieving this deflection. The maximum of the force is represented by the coordinates x2, y1. Until this maximum is reached starting from the relaxed state S1 at zero deflection and force, removal of the force results in the resilient force member 13.1 returning into the relaxed state S1. The maximum at the coordinates x2, y1 represent an equilibrium point for the resilient force member 13.1 to change from the relaxed state S1 into the biased state S2, i.e. the deflection increases further without further increase in force such that the curve arrives at the coordinates x1, y2. At this point, a much lower force than at the maximum is sufficient to hold the resilient force member 13.1 in the biased state S2. Thus, a large amount of energy can be stored by the resilient force member 13.1 in the biased state S2 whilst maintaining a low holding force.

The low holding force in the biased state S2 may cause a small frictional drag on the plunger 10, diverting a small amount of the energy of the drive spring 9 away during medicament delivery, wherein the plunger 10 is moved distally by a release of the energy of the drive spring 9. However, the derived energy is low due to the low holding force.

Figure 6:
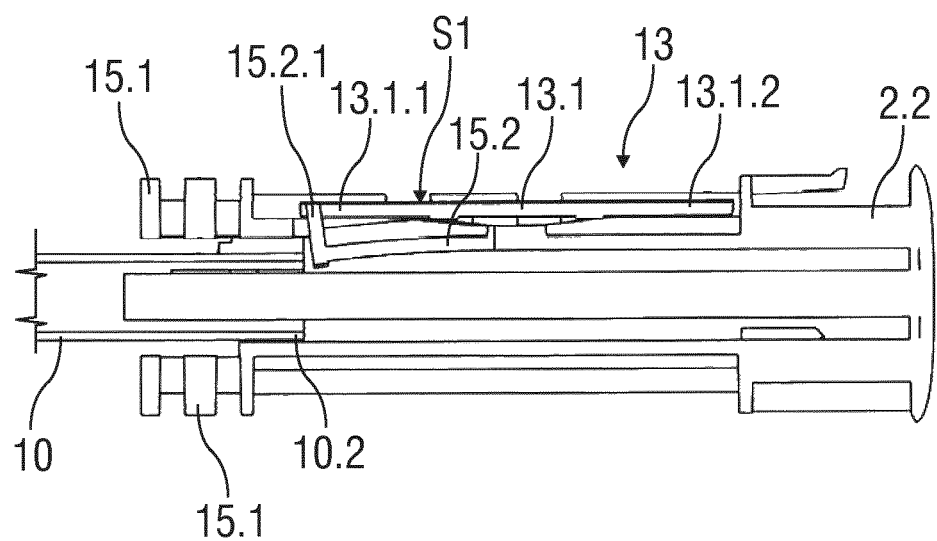
FIG. 6 is a schematic longitudinal section of the drive sub assembly with the audible indicator according to FIG. 4 in a relaxed state.

FIG. 6 shows a longitudinal section of the drive subassembly 1.1 of the drug delivery device 1 comprising the audible indicator 13 according to the first embodiment.

The resilient force member 13.1 is in the relaxed state S1, wherein the drug delivery device 1 is in a state at the end of a medicament delivery process.

For delivering the medicament M through the needle 4 into an injection site, e.g. a patient's skin, the plunger 10 is moved distally from a proximal position to a distal position due to an activation of the drive spring 9. The activation of the drive spring 9 may be initiated by pressing a button or by depressing the needle shroud 7 as it is pushed against the injection site.

In FIG. 6, the plunger 10 has reached the distal position, wherein the flexible arm 15.2 is no longer engaged with the plunger 10. When a proximal end of the plunger 10 passes the distal end of the flexible arm 15.2, the flexible arm 15.2 is allowed to relax and can thus move radially inwards driven by the distally pointing end 13.1.1 of the resilient force member 13.1. As the distally pointing end 13.1.1 of the resilient force member 13.1 moves, the resilient force member 13.1 can transition from a generally biased state S2 into a generally relaxed state S1 releasing stored energy to generate an audible signal, such as a click noise, due to a transition from the second conformation to the first conformation. Due to the large amount of stored energy, the audible signal can be generated with a high intensity, e.g. up to 100 decibels Signals of lesser intensity can also be generated. The proximally pointing end 13.1.2 of the resilient force member 13.1 can also swing radially inwards, thereby hitting the flexible arm 15.2 or the case 2 or another component of the drug delivery device 1. This impact may also contribute to the generation of the audible signal.

The user or patient recognizing the audible signal knows that the medicament delivery process is finished and that the full dose was spent.

The drug delivery device 1 further comprises a carrier 16 to allow an accurate support of the syringe 3 during and after an assembling process. The carrier 16 is adapted to assemble, position and to hold the syringe 3 within the case 2.

FIGS. 7 to 11 respectively show an audible indicator 113 according to a second embodiment.

Figure 7:
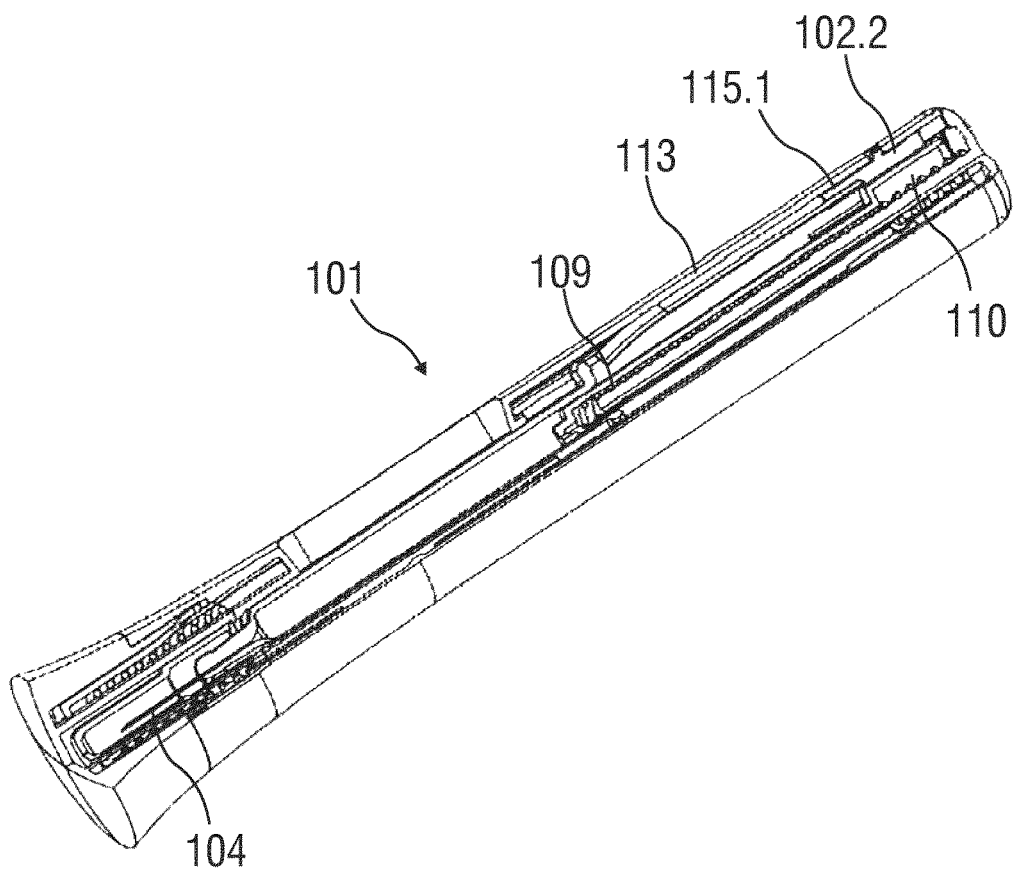
FIG. 7 is a schematic perspective partial section of a drug delivery device comprising an audible indicator according to a second embodiment.

FIG. 7 shows a schematic perspective partial section of an exemplary embodiment of a drug delivery device 101 comprising the audible indicator 113 according to the second embodiment.

The drug delivery device 101 is configured as an autoinjector nearly similar to the description of FIG. 1.

Except for the rear case 102.2 and the audible indicator 113, all components of the drug delivery device 101 have the same configuration as described above in the FIGS. 1 to 6. The audible indicator 113 according to the second embodiment will be described in more detail in FIG. 8. The rear case 102.2 will be described in more detail in FIG. 9.

Figure 8:
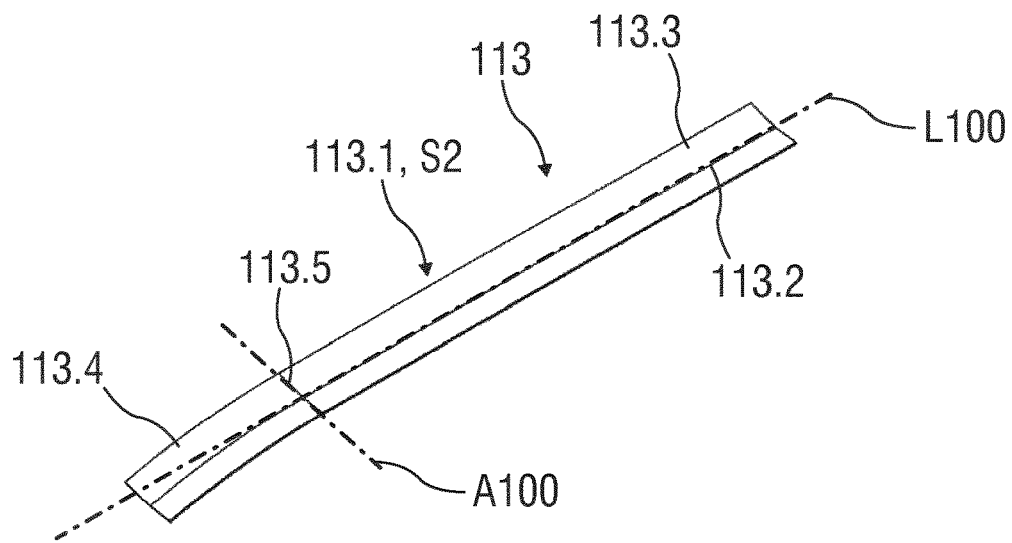
FIG. 8 is a schematic perspective view of the audible indicator according to the second embodiment.

FIG. 8 is a perspective view of the audible indicator 113 according to the second embodiment.

The audible indicator 113 comprises a resilient force member 113.1 that may be configured as a bistable leaf spring comprising a resilient material, e.g. spring steel or spring plastic. Thus, the resilient force member 113.1 is capable of residing in two states. That is, the resilient force member 113.1 may assume two different stable conformations with limited or no application of an external force. For example, these two states can include a first or relaxed state S1 (or pre-assembly state, or trigged state), in which the resilient force member 113.1 has a first conformation. In a second or biased state S2 (or primed state), the resilient force member 113.1 can have a second conformation. The resilient force member 113.1 may comprise a substantially rectangular shape and a longitudinal axis L100 running in parallel to the longest side of the outer circumference of the resilient force member 113.1.

The resilient force member 113.1 further comprises a longitudinal bend 113.2 that is arranged in the center of the resilient force member 113.1 running in parallel to the longitudinal axis L100. The longitudinal bend 113.2 can divide the audible indicator 113 into two wing-shaped sections angled to each other with an angle less than 180 degrees. In the illustrated perspective of FIG. 8, the wing-shaped sections are angled upwards.

The resilient force member 113.1 comprises a proximal spring section 113.3 and a distal spring section 113.4 divided by a cross bend 113.5 running in parallel to an axis A100 that may be perpendicular to the longitudinal axis L100.

According to the present embodiment, the proximal spring section 113.3 is longer than the distal spring section 113.4 with respect to the longitudinal axis L100. In alternative embodiments, the proximal spring section 113.3 may be shorter than the distal spring section 113.4 or have the same length.

The resilient force member 113.1 is coupled to the rear case 102.2 as shown in the following FIG. 9.

Figure 9:
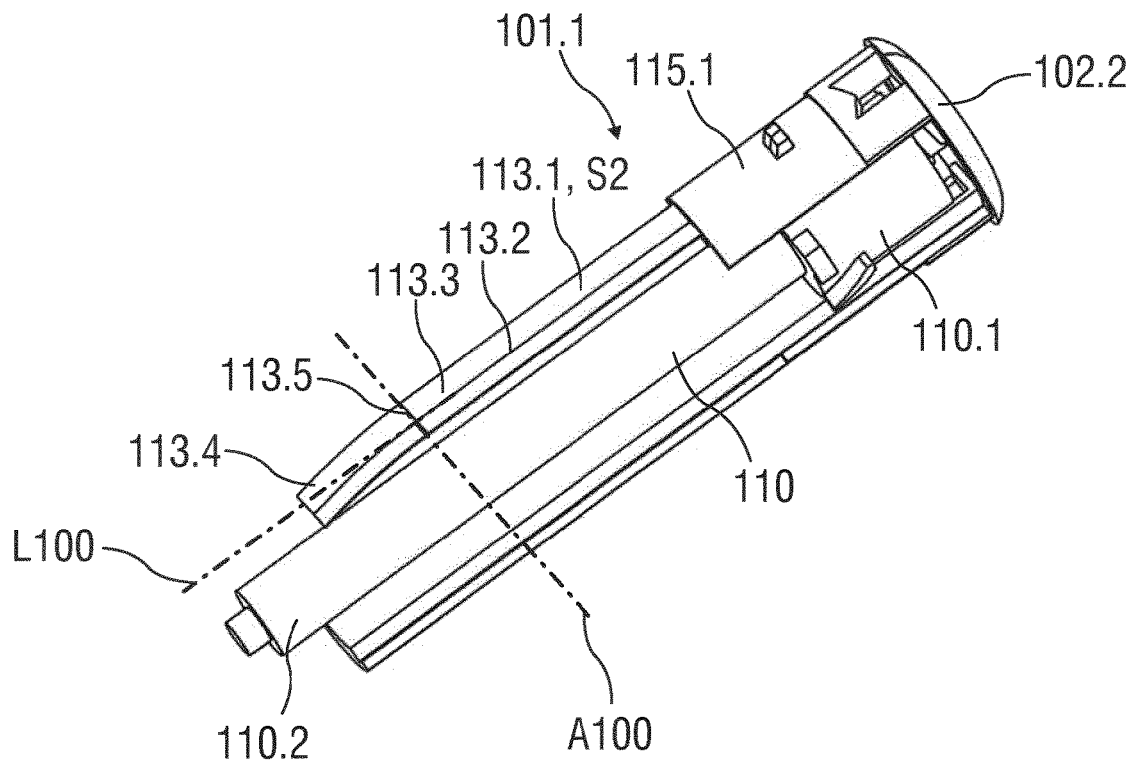
FIG. 9 is a schematic perspective view of a drive sub assembly of the drug delivery device comprising a rear case, a plunger and the audible indicator according to the second embodiment.

FIG. 9 shows a schematic perspective view of an exemplary embodiment of the drive sub assembly 101.1 of the drug delivery device 101.

The rear case 102.2 comprises two support arms 115.1 similar to the ones described in FIG. 4.

According to the present embodiment, the support arms 115.1 are configured with different lengths with respect to the longitudinal axis L100 in an assembled state of the audible indicator 113. In particular, the support arm 115.1 carrying the resilient force member 113.1 is shorter than the other support arm 115.1 in order to create space for arranging the resilient force member 113.1. The resilient force member 113.1 may be coupled to the support arm 115.1 by a positive fit connection. For example, the proximal spring section 113.3 is received within a guiding recess arranged on an inner side of the support arm 115.1 and fixed, e.g. by a snap connection, by welding, gluing or by a frictional fit, wherein a remaining section of the proximal spring section 113.3 and the distal spring section 113.4 project distally from the support arm 115.1.

The illustrated resilient force member 113.1 is in the biased state S2, wherein the distal spring section 113.4 is directed towards the outer circumference of a plunger 110 with respect to the proximal spring section 113.3.

Due to the decreased diameter of a distal plunger section 110.2 (similar to the plunger 10 shown in FIG. 1), the distal spring section 113.4 is radially spaced from the outer circumference of the distal plunger section 110.2. Furthermore, the distal spring section 113.4 is not supported by any component of the drug delivery device 101 as can be seen in FIG. 10.

Figure 10:
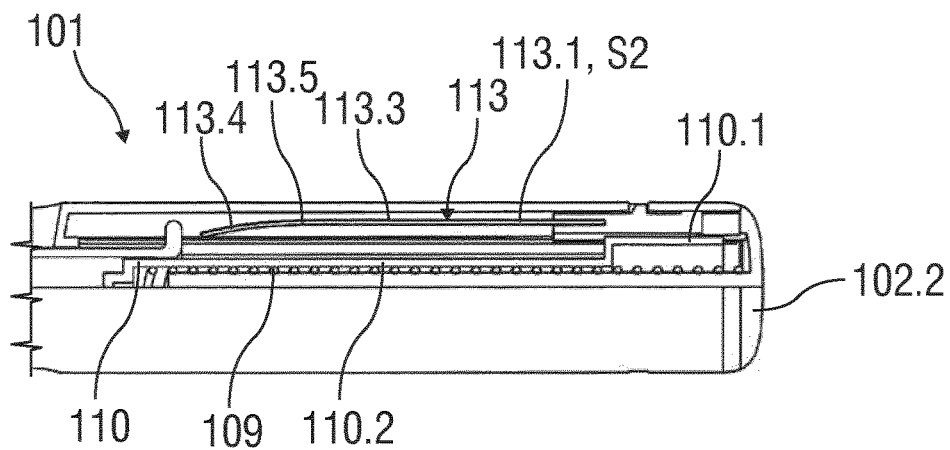
FIG. 10 is a schematic longitudinal section of a proximal part of a drug delivery device in a primed state comprising the audible indicator according to the second embodiment.

FIG. 10 shows a schematic longitudinal section of a proximal part of the drug delivery device 101 comprising the audible indicator 113 according to the second embodiment in the biased state S2, wherein the resilient force member 113.1 stores a certain amount of energy. The plunger 110 is in the proximal position. Thus, the drug delivery device 101 is ready to start a medicament delivery process.

Figure 11:
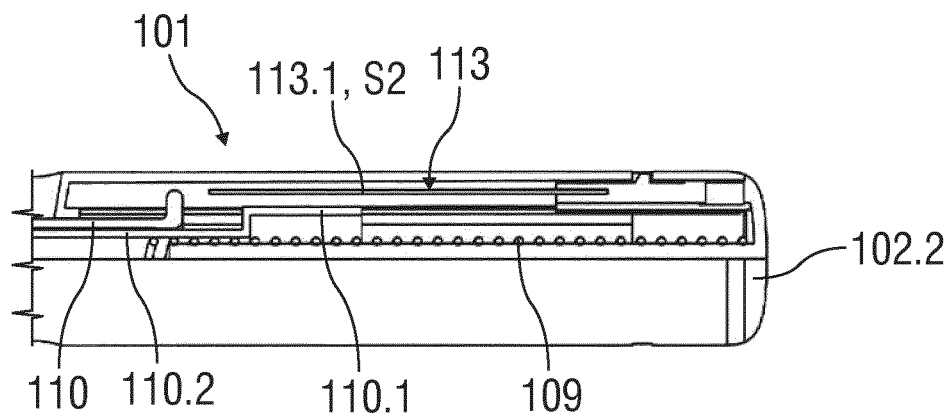
FIG. 11 is a schematic longitudinal section of the proximal part of the drug delivery device with the audible indicator according to FIG. 10 in a relaxed state.

For delivering a medicament M through a needle 104 into an injection site, the plunger 110 has to be moved distally from the proximal position to the distal position as illustrated in FIG. 11 due to the activation of a drive spring 109 as described above.

FIG. 11 shows a schematic longitudinal section of the proximal part of the drug delivery device 101 with the plunger 110 in the distal position and the audible indicator 113 in the relaxed state S1.

At the end of medicament delivery, the proximal plunger section 110.1 abuts the distal spring section 113.4. The abutting generates a force influence on the resilient force member 113.1, which causes the distal spring section 113.5 to deflect radially outwards. As a result, the resilient force member 113.1, in particular the distal spring section 113.4 releases the energy and thus can transition from a generally biased state S2 into a generally relaxed state S1, thereby generating a recognizable audible signal.

FIGS. 12 to 16 respectively show an audible indicator 213 according to a third embodiment.

Figure 12:
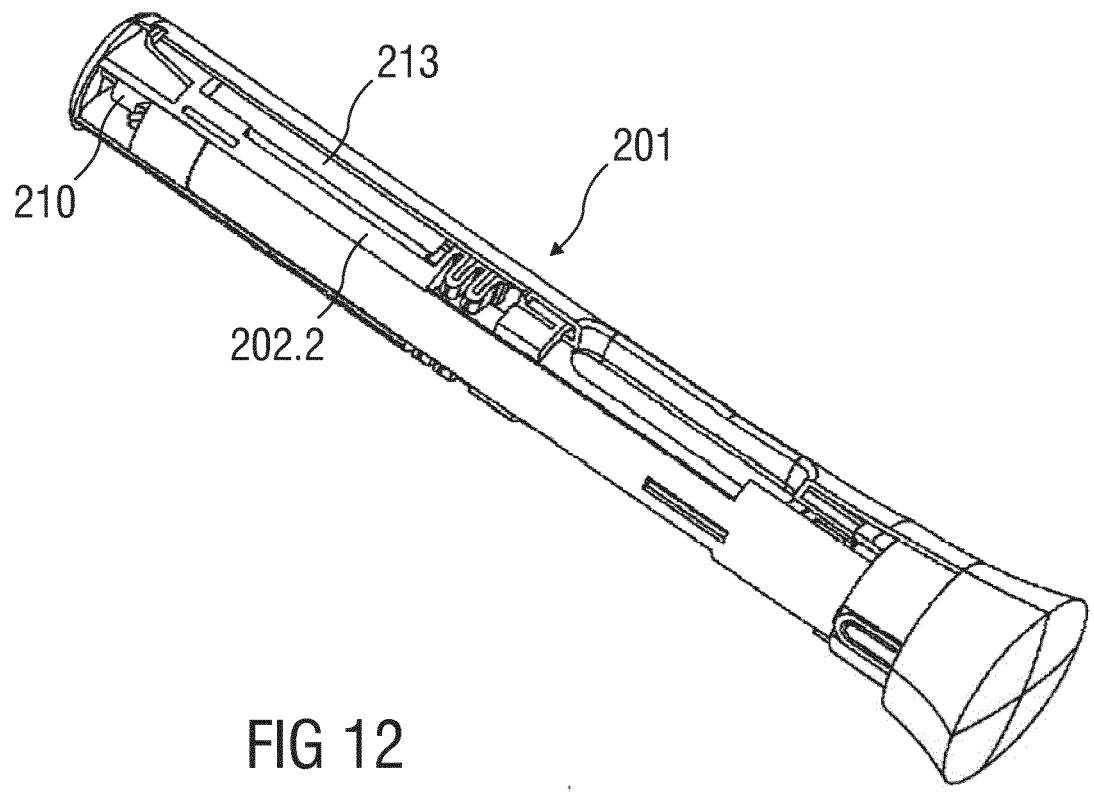
FIG. 12 is a schematic perspective partial section of a drug delivery device comprising an audible indicator according to a third embodiment.

FIG. 12 shows a schematic perspective partial section of an exemplary embodiment of a drug delivery device 201 comprising the audible indicator 213 according to the third embodiment.

The drug delivery device 201 is configured as an autoinjector similar to the one described in FIG. 1.

Except for the rear case 202.2 and the audible indicator 213, all components of the drug delivery device 201 may have the same configuration as described above in the FIGS. 1 to 6. The audible indicator 213 according to the third embodiment will be described in more detail in FIG. 13. The rear case 202.2 will be described in more detail in FIG. 14.

Figure 13:
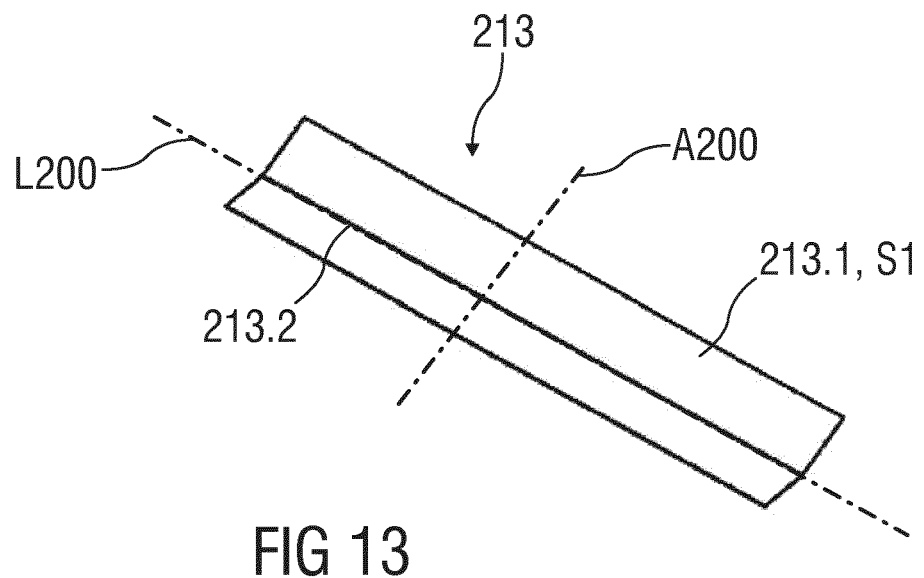
FIG. 13 is a schematic perspective view of the audible indicator according to the third embodiment in a pre-assembled state.

FIG. 13 is a perspective view of the audible indicator 213 according to the second embodiment.

The audible indicator 213 comprises a resilient force member 213.1 that is configured as a bistable leaf spring comprising a resilient material, e.g. spring steel or spring plastic. Thus, the resilient force member 213.1 is capable of residing in two states. That is, the resilient force member 213.1 may assume two different stable conformations with limited or no application of an external force. For example, these two states can include a first or relaxed state S1 (or pre-assembly state, or trigged state), in which the resilient force member 213.1 has a first conformation. In a second or biased state S2 (or primed state), the resilient force member 213.1 can have a second conformation. The resilient force member 213.1 may comprise a substantially rectangular shape and a longitudinal axis L200 running in parallel to the longest side of the outer circumference of the resilient force member 213.1.

The resilient force member 213.1 further comprises a longitudinal bend 213.2 that may be arranged generally in the center of the resilient force member 213.1 running in parallel to the longitudinal axis L200. The longitudinal bend 213.2 divides the resilient force member 213.1 into two wing-shaped sections angled to each other with an angle less than 180 degrees. In the illustrated perspective view of FIG. 13, the wing-shaped sections are angled upwards.

The resilient force member 213.1 is coupled to the rear case 202.2 as shown and described in the following FIG. 14.

Figure 14:
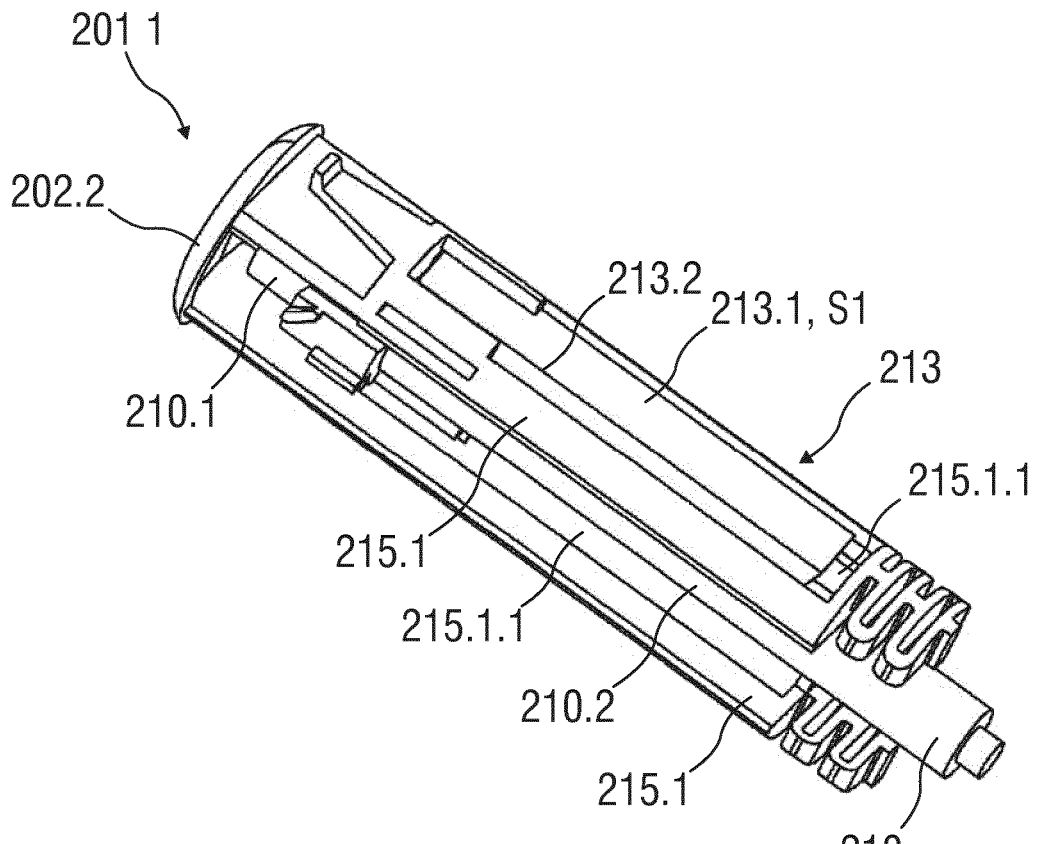
FIG. 14 is a schematic perspective view of a drive sub assembly of the drug delivery device comprising a rear case, a plunger and the audible indicator according to the third embodiment.

FIG. 14 shows a schematic perspective view of an exemplary embodiment of a drive sub assembly 201.1 of the drug delivery device 201.

The rear case 202.2 comprises two support arms 215.1 nearly similar to the ones shown in FIG. 4.

According to the present embodiment, the support arms 215.1 have the same lengths with respect the longitudinal axis L200 in an assembled state of the audible indicator 213. The support arms 215.1 respectively comprise a longitudinal recess 215.1.1, wherein the resilient force member 213.1 is arranged within the longitudinal recess 215.1.1 of one of the support arms 215.1. Thus, the resilient force member 213.1 may be proximally fixed to the support arm 215.1 by a positive connection, e.g. a snap connection, in order to prevent rotation of the resilient force member 213.1.

The wing-shaped sections of the resilient force member 213.1 are bent upwards away from a plunger 210.

Figure 15:
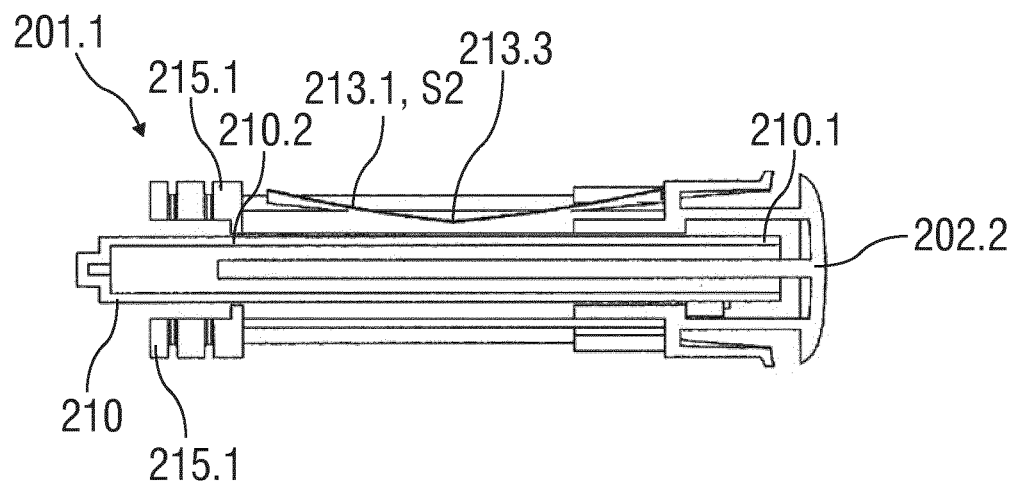
FIG. 15 is a schematic longitudinal section of the drive subassembly comprising the audible indicator according to the third embodiment in a primed state.

For assembling the audible indicator 213 into the drug delivery device 201, the resilient force member 213.1 is additionally bent in the center about the axis A200 until a kink tip 213.3 is generated and the resilient force member 213.1 can transition from a generally relaxed state S1 into a generally biased state S2 as illustrated in FIG. 15, wherein the kink tip 213.3 points towards the outer circumference of the plunger 210. This bending may be achieved by applying a predetermined force onto the center point of the resilient force member 213.1. Likewise, this bending may be achieved by supporting the proximal end of the resilient force member 213.1 close to the kink point and applying a predetermined force, e.g. 20 N to the distal end of the resilient force member 213.1. The kink tip 213.3 may be only achieved if the longitudinal bend 213.2 has a sufficiently small angle and bend radius and if a sufficiently small bend radius and sufficiently large deflection are applied when generating the kink tip 213.3.

FIG. 15 shows a schematic longitudinal section of the drive sub assembly 201.1 comprising the audible indicator 213 according to the third embodiment in the biased state S2, wherein the resilient force member 213.1 stores a certain amount of energy. The plunger 10 is in the proximal position and the kink tip 213.3 is supported by the outer circumference of the plunger 210. The drug delivery device 201 is ready to start a medicament delivery process.

Figure 16:
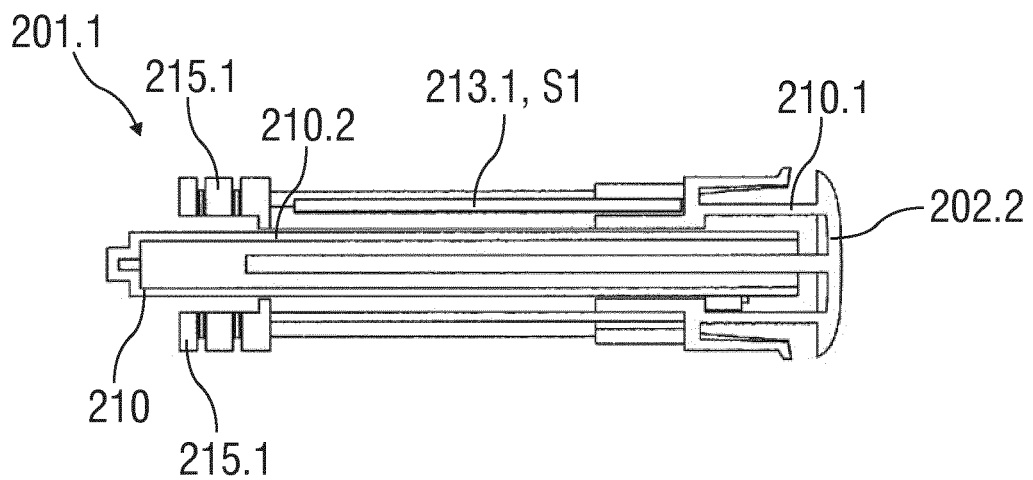
FIG. 16 is a schematic longitudinal section of the drive sub assembly according to FIG. 15 comprising the audible indicator according to the third embodiment in a relaxed state.

For delivering a medicament M into an injection site, the plunger 210 has to be moved distally from the proximal position to the distal position as illustrated in FIG. 16.

At the end of medicament delivery, when the plunger 10 passes the kink tip 213.3 distally, a proximal plunger section 210.1 with an increased diameter with respect to a distal plunger section 210.1, the kink tip 213.3 generates a force influence on the resilient force member 213.1, which causes the kink tip 213.3 to deflect radially outwards as illustrated in FIG. 16.

FIG. 16 shows a schematic longitudinal section of the drive sub assembly 201.1 with the plunger 210 in the distal position and the audible indicator 213 in the relaxed state S1.

Due to the deflection of the kink tip 213.3, the energy is released from the resilient force member 213.1, whereby the resilient force member 213.1 is straightened with respect to the longitudinal axis L200. By releasing the stored energy, the resilient force member 213.1 can transition from a generally biased state S2 into a generally relaxed state S1, thereby generating a recognizable audible signal.

FIGS. 17 to 22 respectively show an audible indicator 313 according to a fourth embodiment.

Figure 17:
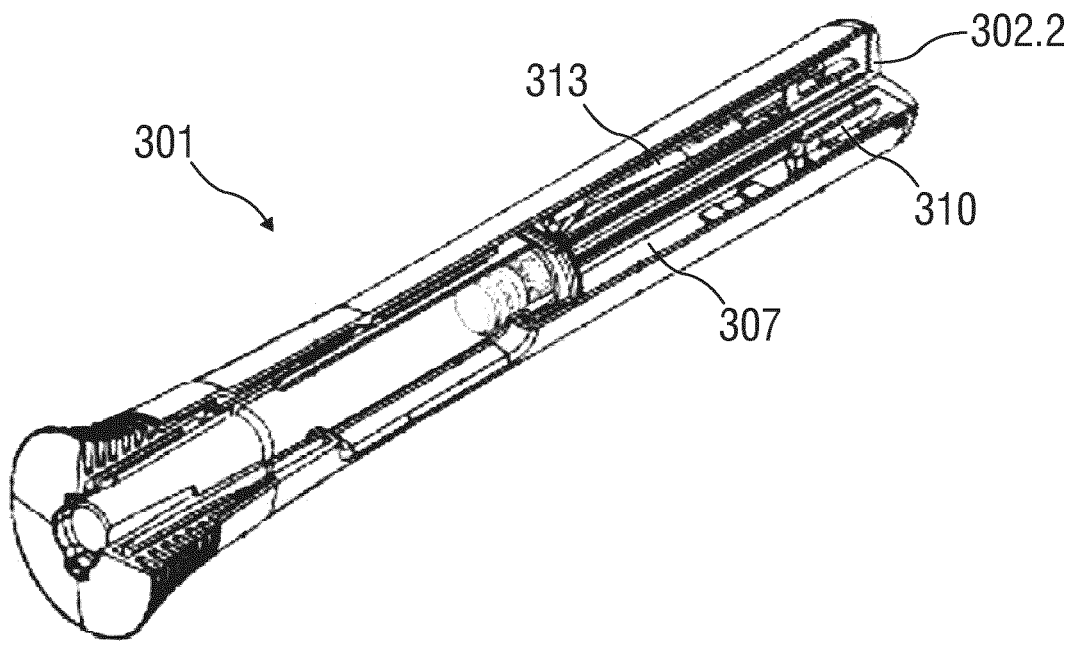
FIG. 17 is a schematic perspective partial section of a drug delivery device comprising an audible indicator according to a fourth embodiment.

FIG. 17 shows a schematic perspective partial section of an exemplary embodiment of a drug delivery device 301 comprising the audible indicator 313 according to a fourth embodiment.

The drug delivery device 301 is configured as an autoinjector similar to the one described in FIG. 1.

Except for the rear case 302.2 and the audible indicator 313, all components of the drug delivery device 301 have the same configuration as described above in the FIGS. 1 to 6. The audible indicator 313 according to the fourth embodiment will be described in more detail in FIG. 18. The rear case 302.2 will be described in more detail in FIG. 19.

Figure 18:
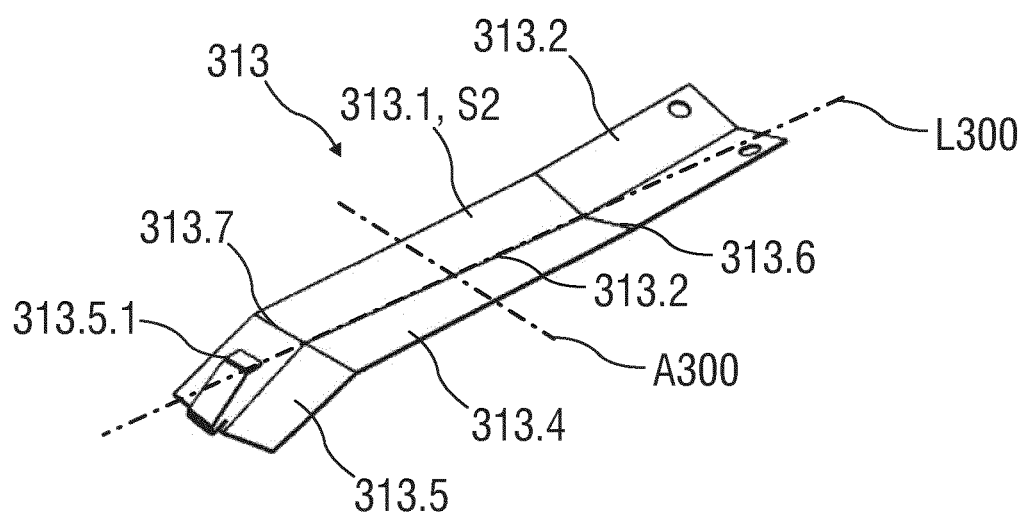
FIG. 18 is a schematic perspective view of the audible indicator according to the fourth embodiment in a pre-assembled state.

FIG. 18 is a perspective view of the audible indicator 313 according to the fourth embodiment.

The audible indicator 313 comprises a resilient force member 313.1 that is configured as a bistable leaf spring comprising a resilient material, e.g. spring steel or spring plastic. Thus, the resilient force member 313.1 is capable of residing in two states. That is, the resilient force member 313.1 may assume two different stable conformations with limited or no application of an external force. For example, these two states can include a first or relaxed state S1 (or pre-assembly state, or trigged state), in which the resilient force member 313.1 has a first conformation. In a second or biased state S2 (or primed state), the resilient force member 313.1 can have a second conformation. The resilient force member 313.1 may comprise a substantially rectangular shape and a longitudinal axis L300 running in parallel to the longest side of the outer circumference of the resilient force member 313.1.

The resilient force member 313.1 further comprises a longitudinal bend 313.2 that can be arranged generally in the center of the resilient force member 313.1 running in parallel to the longitudinal axis L300. The longitudinal bend 313.2 can divide the resilient force member 313.1 into two wing-shaped sections angled to each other with an angle less than 180 degrees.

The resilient force member 313.1 may be further divided into a proximal spring section 313.3, an intermediate spring section 313.4 and a distal spring section 313.5 due to a first cross bend 313.6 and a second cross bend 313.7 respectively running in parallel to an axis A300 that may be perpendicular to the longitudinal axis L300.

Additionally, the distal spring section 313.5 comprises a hook-like projection 313.5.1 arranged on a distal end of the distal spring section 313.5 and protruding diagonally towards a proximal end of the distal spring section 313.5.

Figure 19:
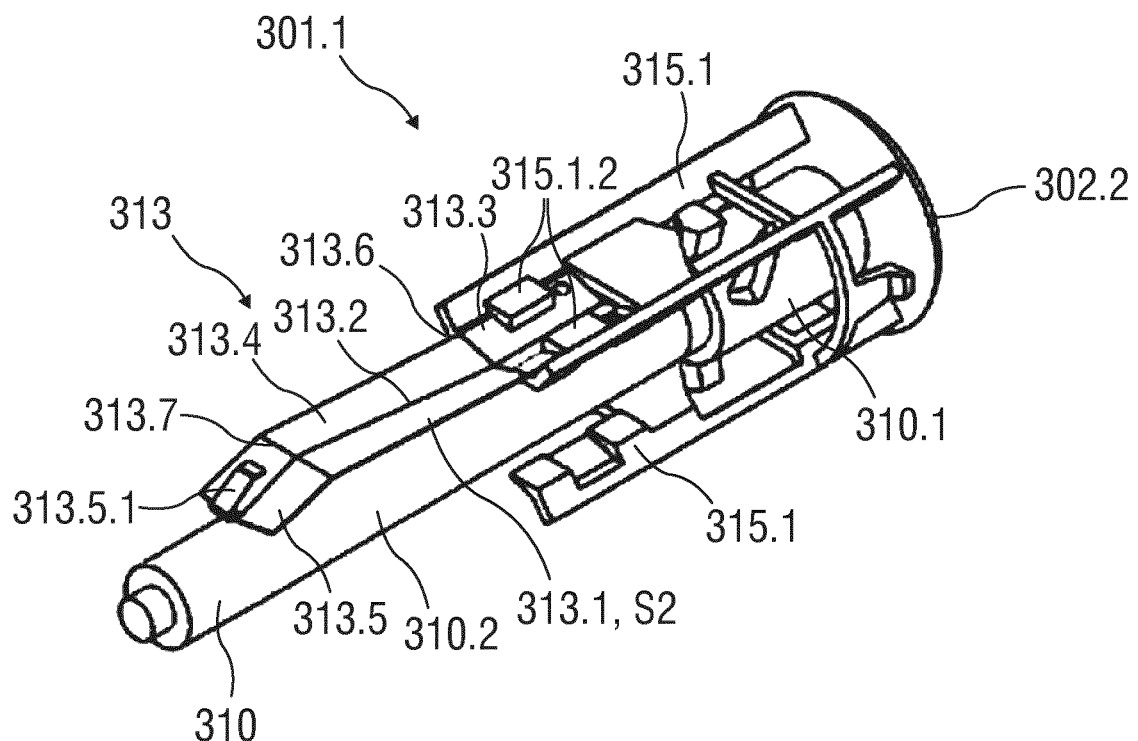
FIG. 19 is a schematic perspective view of a drive sub assembly of the drug delivery device comprising a rear case, a plunger and the audible indicator according to the fourth embodiment.

The resilient force member 313.1 is coupled to the rear case 302.2 as illustrated in FIG. 19.

FIG. 19 shows a schematic perspective view of a drive sub assembly 301.1 of the drug delivery device 1 comprising the rear case 302.2, a plunger 310 and the audible indicator 313 according to the fourth embodiment.

The rear case 302.2 comprises two support arms 315.1 nearly similar to the ones described in FIG. 4.

According to the present embodiment, the support arms 315.1 have the same length with respect to the longitudinal axis L300 in an assembled state of the audible indicator 313. Alternatively, the support arm 315.1 which is not connected to the resilient force member 313.1 could be any length. The support arms 315.1 respectively comprise a guiding recess 315.1.1, wherein the resilient force member 313.1 is received within the guiding recess 315.1.1 of one of the support arms 315.1. Particularly, the proximal spring section 313.3 is arranged within the guiding recess 315.1.1, which may comprise guiding tracks for a positive locking of the resilient force member 313.1. The arrangement of the proximal spring section 313.3 within the guiding recess 315.1.1 is supported by two locking tabs 315.1.2 that decrease a cross section of the guiding recess 315.1.1 radially above the proximal spring section 313.3.

Figure 20:
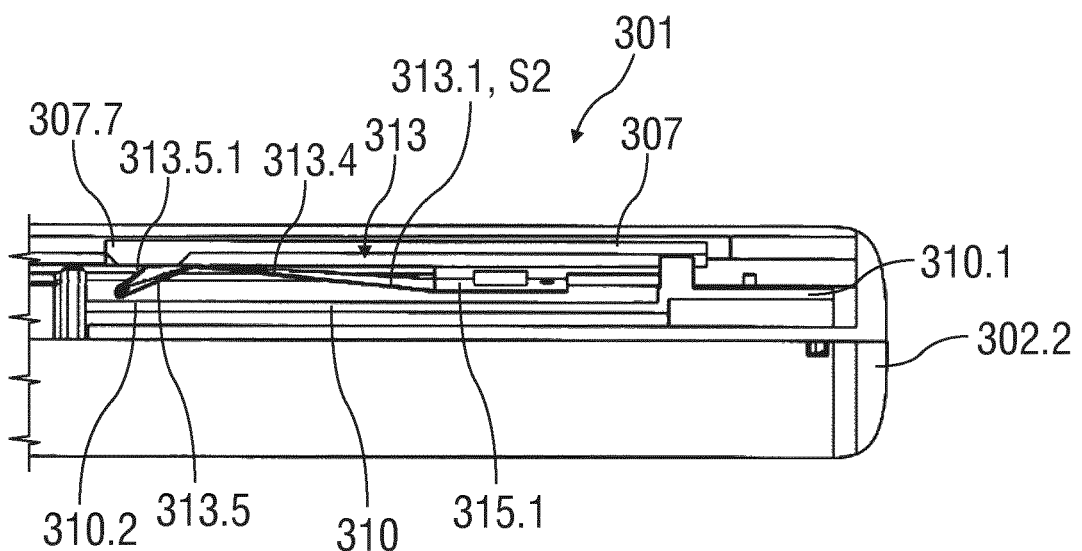
FIG. 20 is a schematic longitudinal section of a proximal part of a drug delivery device in an initial state comprising the audible indicator according to the fourth embodiment in a biased state.

The intermediate spring section 313.4 and the distal spring section 313.5 projects distally from the support arm 315.1, wherein the intermediate spring section 313.4 is angled with respect to the proximal spring section 313.3 radially outwards as best shown in FIG. 20. The distal spring section 313.5 is angled radially inwards with respect to the intermediate spring section 313.4 and thus bent towards the plunger 310 as illustrated in FIG. 20. By bending the distal spring section 313.5 radially inwards, the resilient force member 313.1 can transition from the relaxed state S1 into the biased state, thereby storing energy.

FIG. 20 shows a schematic longitudinal section of a proximal part of the drug delivery device 1 comprising the audible indicator 313 according to the fourth embodiment in the biased state S2, wherein the drug delivery device 301 is in an initial state prior to medicament delivery.

The resilient force member 313.1 is supported by a supporting rib 307.7 arranged within an inner circumference of a needle shroud 307. In particular, the hook-like projection 313.5.1 abuts against the supporting rib 307.7. Thus, the engagement between the hook-like projection 313.5.1 and the supporting rib 307.7 prevents a premature activation of the resilient force member 313.1 during storage and transportation. Alternatively, there may be arranged more than one supporting rib 307.7

Figure 21:
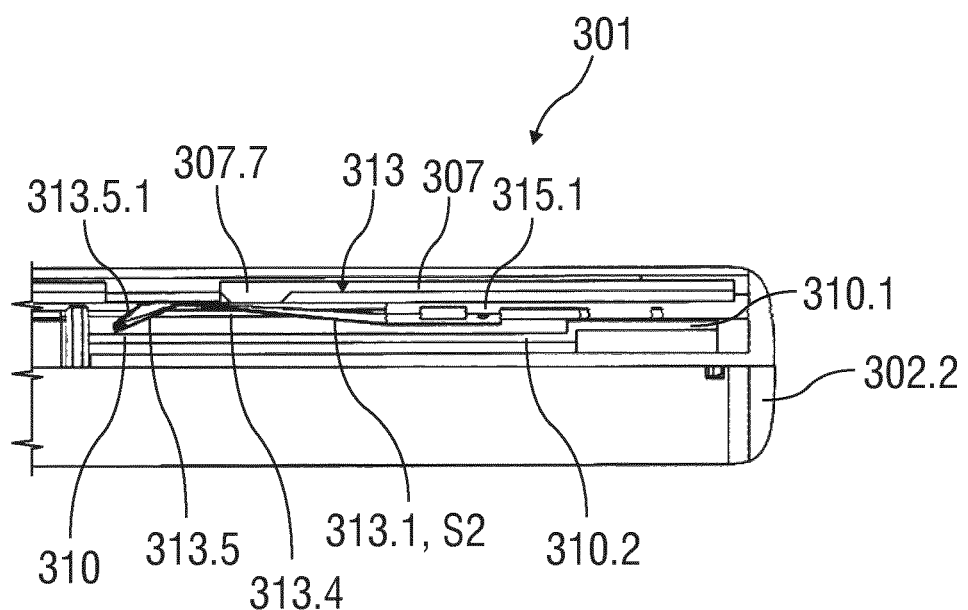
FIG. 21 is a schematic longitudinal section of the proximal part of the drug delivery device in a primed state with the audible indicator according to FIG. 20 in the biased state.

FIG. 21 shows a schematic longitudinal section of the proximal part of the drug delivery device 301 comprising the audible indicator 313 according to the fourth embodiment in the biased state S2, wherein the drug delivery device 301 is in a primed state.

Figure 22:
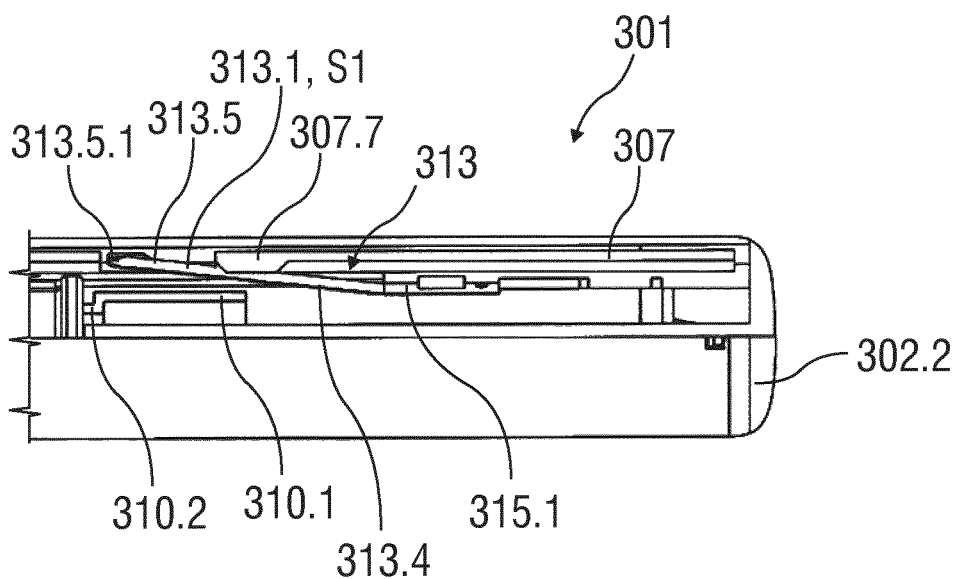
FIG. 22 is a schematic longitudinal section of the proximal part of the drug delivery device with the audible indicator according to FIG. 20 in a relaxed state.

Hereby, the drug delivery device 301 is primed for medicament delivery and thus ready to use. During priming, the needle shroud 307 was moved proximally into a case 302, thus the supporting rib 307.7 moves proximally behind the hook-like projection 313.5.1, thereby generating space for the distal spring section 313.5 to deflect radially outwards as illustrated in FIG. 22. The plunger 310 is in the proximal position, the drug delivery device 301 is ready to start medicament delivery.

For delivering a medicament M into an injection site, the plunger 310 has to be moved distally from the proximal position to the distal position as illustrated in FIG. 22.

FIG. 22 shows a schematic longitudinal section of the proximal part of the drug delivery device 301 with the audible indicator 313 in the relaxed state S1 after medicament delivery.

At the end of medicament delivery, the proximal plunger section 310.1 abuts the distal spring section 313.5. The abutting generates a force influence on the resilient force member 313.1, which causes the distal spring section 313.5 to deflect radially outwards.

Due to the deflection of the distal spring section 313.5, the energy is released from the resilient force member 313.1. By releasing the stored energy, the resilient force member 313.1 can transition from a generally biased state S2 into a generally relaxed state S1, thereby generating a recognizable audible signal.

FIGS. 23 to 30 respectively show an audible indicator 413 according to a fifth embodiment.

Figure 23:
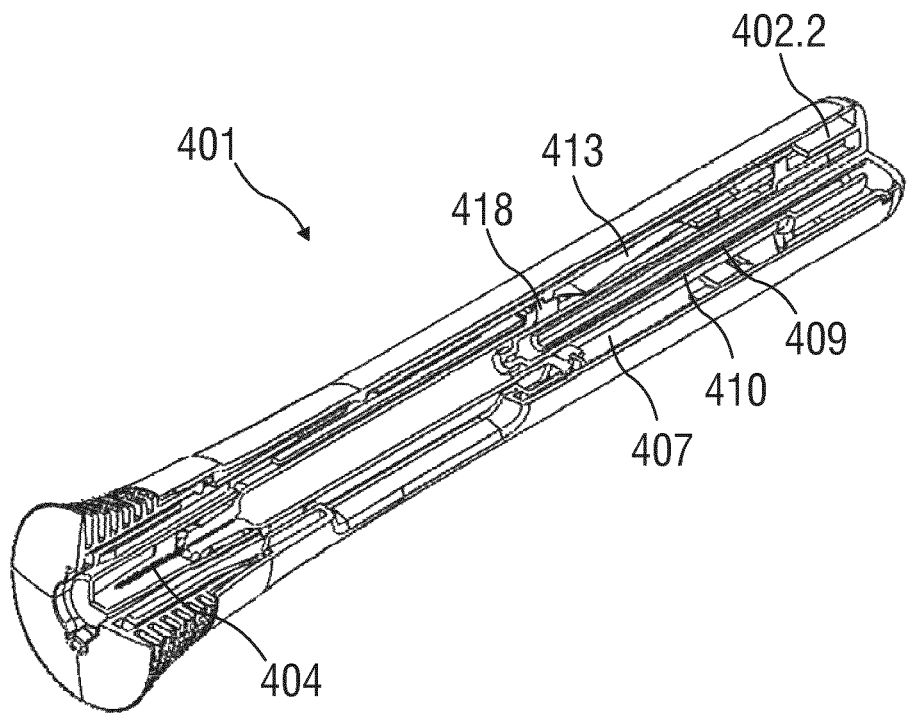
FIG. 23 is a schematic perspective partial section of a drug delivery device comprising an audible indicator according to a fifth embodiment.

FIG. 23 is a schematic perspective partial section of an exemplary embodiment of a drug delivery device 401 comprising the audible indicator 413 according to the fifth embodiment.

The drug delivery device 401 is configured as an autoinjector similar to the one described in FIG. 1.

Except for the rear case 402.2 and the audible indicator 413, all components of the drug delivery device 401 substantially have the same configuration as described above in the FIGS. 1 to 6. The audible indicator 413 according to the fifth embodiment will be described in more detail in FIG. 24. The rear case 402.2 will be described in more detail in FIG. 26.

Figure 24:
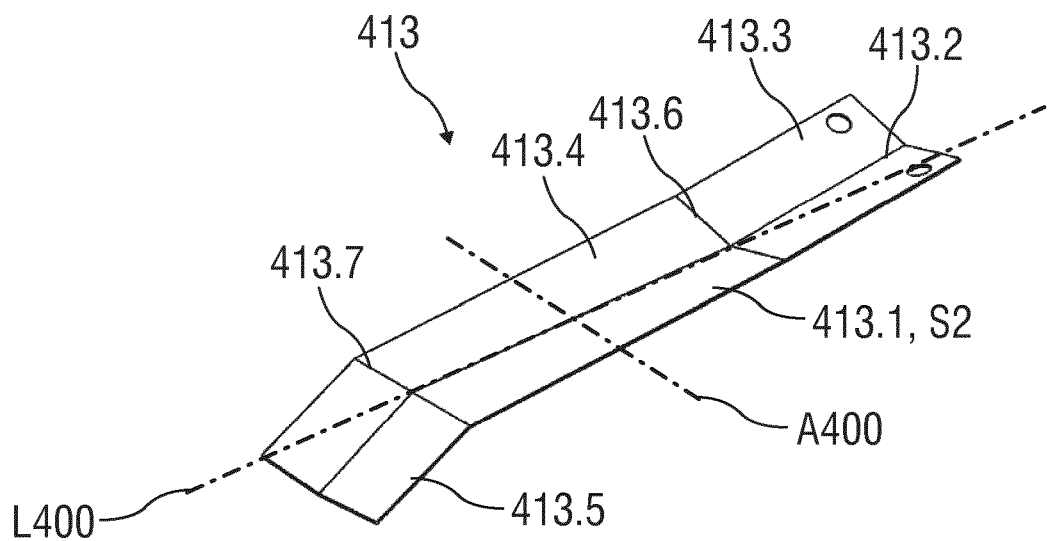
FIG. 24 is a schematic perspective view of the audible indicator according to the fifth embodiment in a pre-assembled state.

FIG. 24 is a perspective view of the audible indicator 413 according to the fifth embodiment.

The audible indicator 413 comprises a resilient force member 413.1 that is configured as a bistable leaf spring comprising a resilient material, e.g. spring steel or spring plastic. Thus, the resilient force member 413.1 is capable of residing in two states. That is, the resilient force member 413.1 may assume two different stable conformations with limited or no application of an external force. For example, these two states can include a first or relaxed state S1 (or pre-assembly state, or trigged state), in which the resilient force member 413.1 has a first conformation. In a second or biased state S2 (or primed state), the resilient force member 413.1 can have a second conformation. The resilient force member 413.1 may comprise a substantially rectangular shape and a longitudinal axis L400 running in parallel to the longest side of the outer circumference of the resilient force member 413.1.

The resilient force member 413.1 further comprises a longitudinal bend 413.2 that can be arranged generally in the center of the resilient force member 413.1 running in parallel to the longitudinal axis L400. The longitudinal bend 413.2 can divide the resilient force member 413.1 into two wing-shaped sections angled to each other with an angle less than 180 degrees.

The resilient force member 413.1 can be further divided into a proximal spring section 413.3, an intermediate spring section 413.4 and a distal spring section 413.5 due to a first cross bend 413.6 and a second cross bend 413.7 respectively running in parallel to an axis A400 that can be perpendicular to the longitudinal axis L400.

According to FIG. 24, the resilient force member 413.1 is in the biased state S2, wherein the distal spring section 413.5 is bent radially inwards with respect to the intermediate spring section 413.4 over the second cross bend 413.7.

Figure 26:
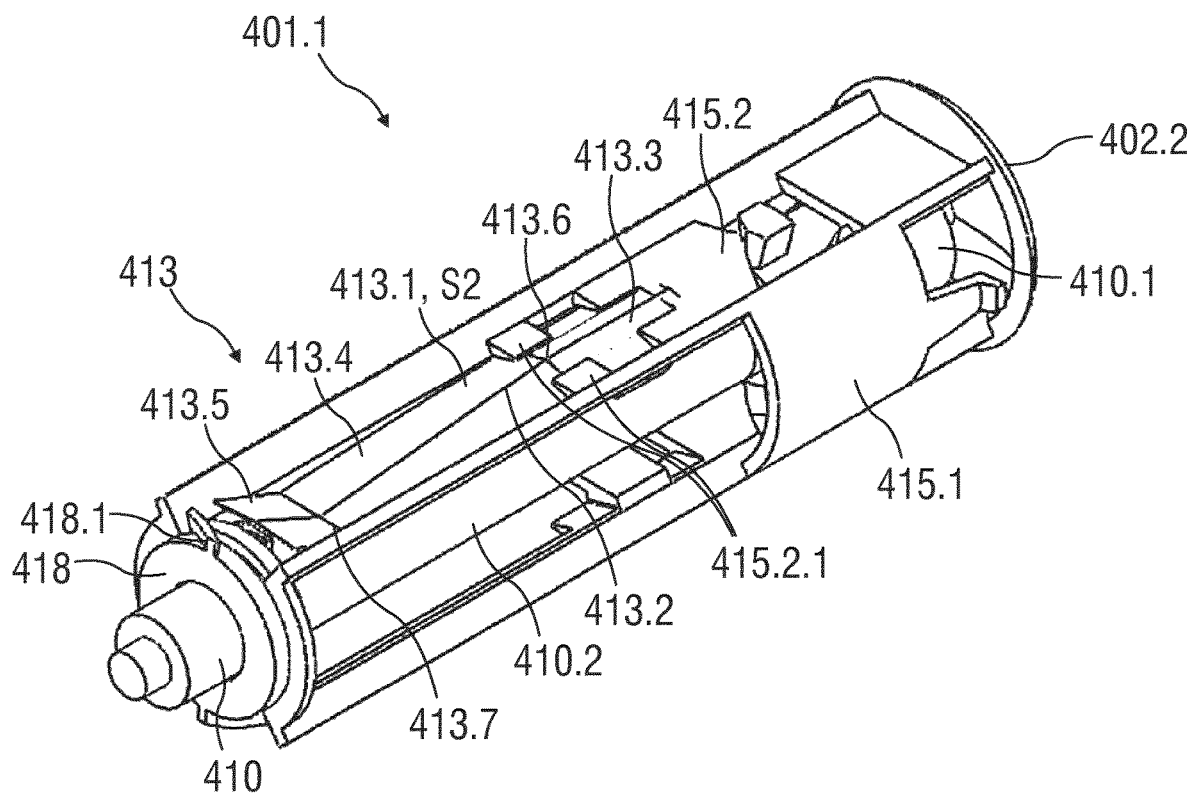
FIG. 26 is a schematic perspective view of a drive sub assembly of the drug delivery device comprising a rear case, a plunger, the collar according to FIG. 25 and the audible indicator according to the fifth embodiment.

The resilient force member 413.1 is coupled to the rear case 402.2 as illustrated in FIG. 26.

Figure 25:
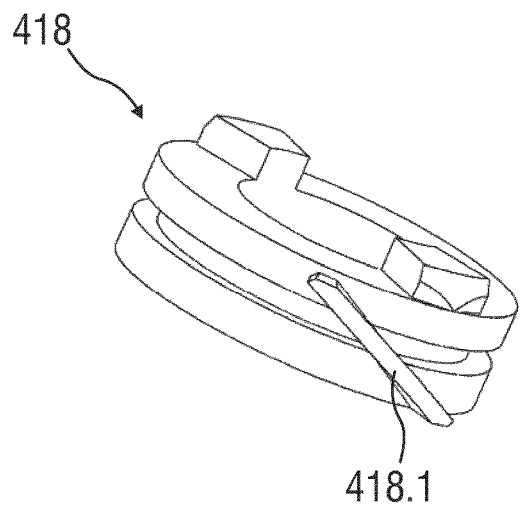
FIG. 25 is a schematic perspective view of a collar.

FIG. 25 shows a schematic perspective view of a collar 418 that is assembled to a drive sub assembly 401.1 as illustrated in FIG. 26.

The collar 418 comprises a collar ramp 418.1 that is arranged on an outer circumference of the collar 418 and configured as a diagonally ramped surface.

FIG. 26 shows a schematic perspective view of the drive sub assembly 401.1 of the drug delivery device 401 comprising the rear case 402.2, a plunger 410, the audible indicator 413 according to the fifth embodiment and the collar 418.

The rear case 402.2 comprises two support arms 415.1 similar to the ones described in FIG. 4.

According to the present embodiment, the support arms 415.1 have the same length with respect to the longitudinal axis L400 in an assembled state of the audible indicator 413. A fixing element 415.2 is arranged between the support arms 415.1 in order to receive the resilient force member 413.1.

Figure 27:
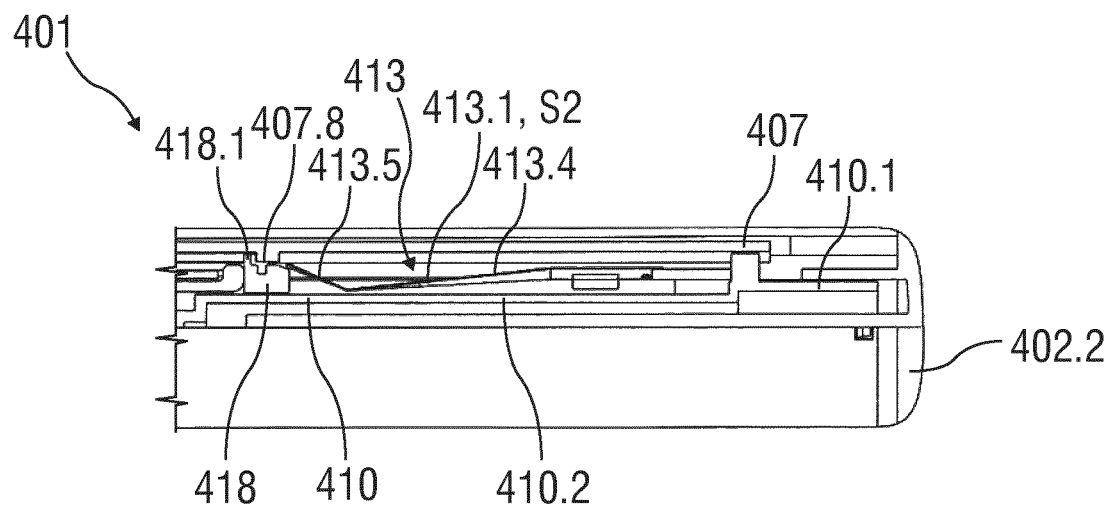
FIG. 27 is a schematic longitudinal section of a proximal part of a drug delivery device in an initial state comprising the audible indicator according to the fifth embodiment in a biased state.

The intermediate spring section 413.4 and the distal spring section 413.5 project distally from the fixing element 415.2, wherein the intermediate spring section 413.4 is angled with respect to the proximal spring section 413.3 radially inwards. The distal spring section 413.5 is angled radially outwards with respect to the intermediate spring section 413.4 and thus bent away from the plunger 410 as illustrated in FIG. 27. By bending the distal spring section 413.5 radially outwards, the resilient force member 413.1 can transition from a generally relaxed state S1 into a generally biased state S2, thereby storing energy.

The resilient force member 413.1, in particular the bent distal spring section 413.5 is supported by an outer circumference of the collar 418 that is coupled distally with a distal plunger section 410.2, e.g. by a threaded connection. Thus, the engagement between the distal spring section 413.5 and the collar 418 prevents a premature activation of the resilient force member 413.1 during storage and transportation.

FIG. 27 shows a schematic longitudinal section of a proximal part of the drug delivery device 401 comprising the audible indicator 413 according to the fifth embodiment in the biased state S2, wherein the drug delivery device 401 is in an initial state prior to medicament delivery.

Figure 28:
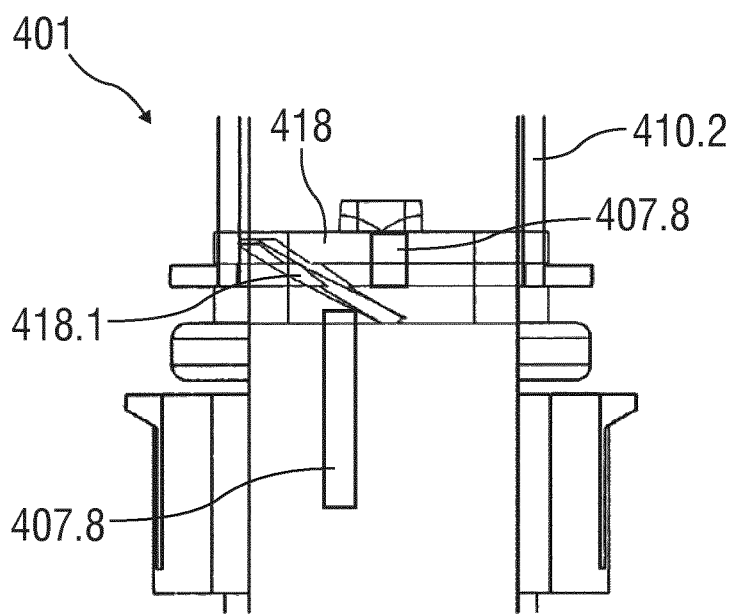
FIG. 28 is a schematic longitudinal section of a cut out of the drug delivery device according to FIG. 23 with the collar according to FIG. 25.

The collar 418 is prevented against rotation by a number of locking ribs 407.8 as illustrated in FIG. 28.

FIG. 28 shows a schematic longitudinal detail section of the drug delivery device 401 according to FIG. 27 illustrating the collar 418 and the number of locking ribs 407.8.

According to the illustrated embodiment, a needle shroud 407 is arranged that comprises two locking ribs 407.8 arranged on an inner circumference of the needle shroud 407. Alternatively, there may be arranged only one or more than two locking ribs 407.8.

The locking ribs 407.8 extends in parallel to a longitudinal extension of the drug delivery device 1 and projects radially inwards, whereby the collar ramp 418.1 projects between the locking ribs 407.8 thus preventing a rotational movement of the collar 418 with respect to the needle shroud 407 during storage and transportation.

During priming of the drug delivery device 401, a force is required to move the needle shroud 407 proximally with respect to the rear case 402.2. As a result, the locking ribs 407.8 move along the collar ramp 418.1. This movement causes a rotation of the collar 418 with respect to the plunger 410. Due to the threaded connection, the collar 418 is moved distally with respect to the resilient force member 413.1 and the bent distal spring section 413.5 is unsupported as illustrated in FIG. 29.

Figure 29:
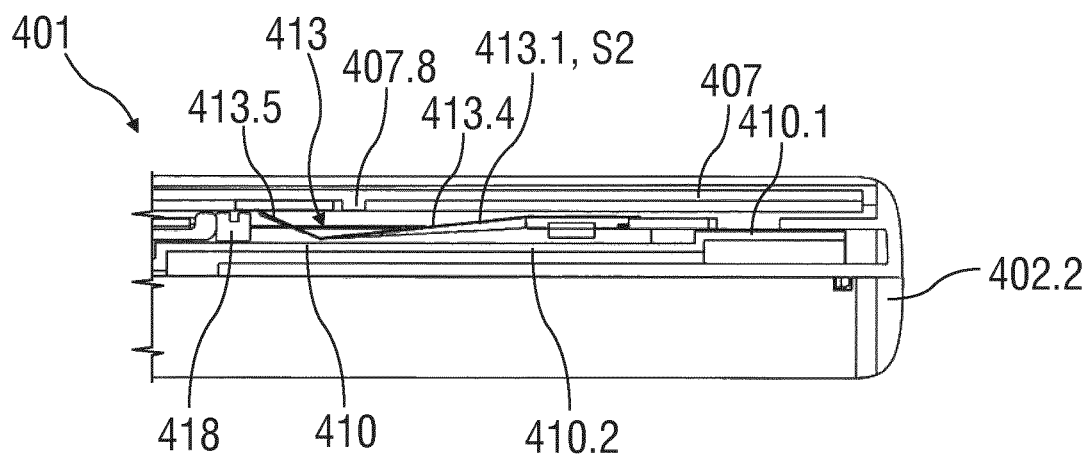
FIG. 29 is a schematic longitudinal section of the proximal part of the drug delivery device in a primed state with the audible indicator according to FIG. 27.

FIG. 29 shows a schematic longitudinal section of the proximal part of the drug delivery device 1 comprising the audible indicator 413 according to the fifth embodiment in the biased state S2, wherein the drug delivery device 401 is in the primed state and the distal spring section 413.5 is unsupported.

Thus, the drug delivery device 401 is ready to start medicament delivery.

Figure 30:
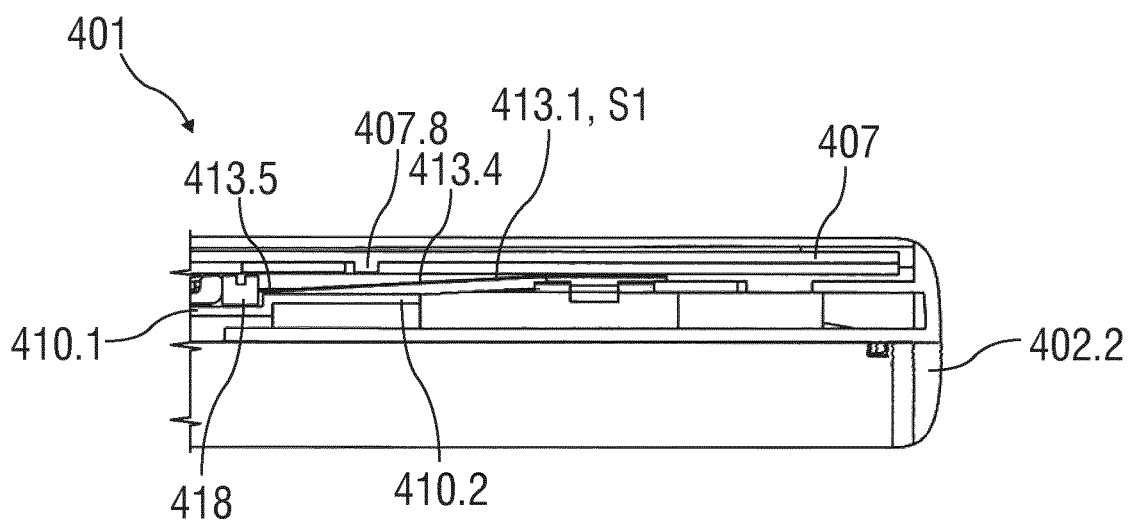
FIG. 30 is a schematic longitudinal section of the proximal part of the drug delivery device with the audible indicator according to FIG. 27 in a relaxed state.

For delivering a medicament M through a needle 404 into an injection site, the plunger 410 has to be moved distally from the proximal position to the distal position as illustrated in FIG. 30 due to the activation of a drive spring 409 as described above.

FIG. 30 shows a schematic longitudinal section of the proximal part of the drug delivery device 401 with the audible indicator 413 in the relaxed state S1 after medicament delivery.

At the end of medicament delivery, a proximal plunger section 410.1 with an increased diameter with respect to the distal plunger section 410.2 abuts the distal spring section 413.5. The abutting generates a force influence on the resilient force member 413.1, which causes the distal spring section 413.5 to deflect radially inwards.

Due to the deflection of the distal spring section 413.5, the energy is released from the resilient force member 413.1. By releasing the stored energy, the resilient force member 413.1 can transition from a generally biased state S2 into a generally relaxed state S1, thereby generating a recognizable audible signal.

FIGS. 31 to 35 respectively show an audible indicator 513 according to a sixth embodiment.

Figure 31:
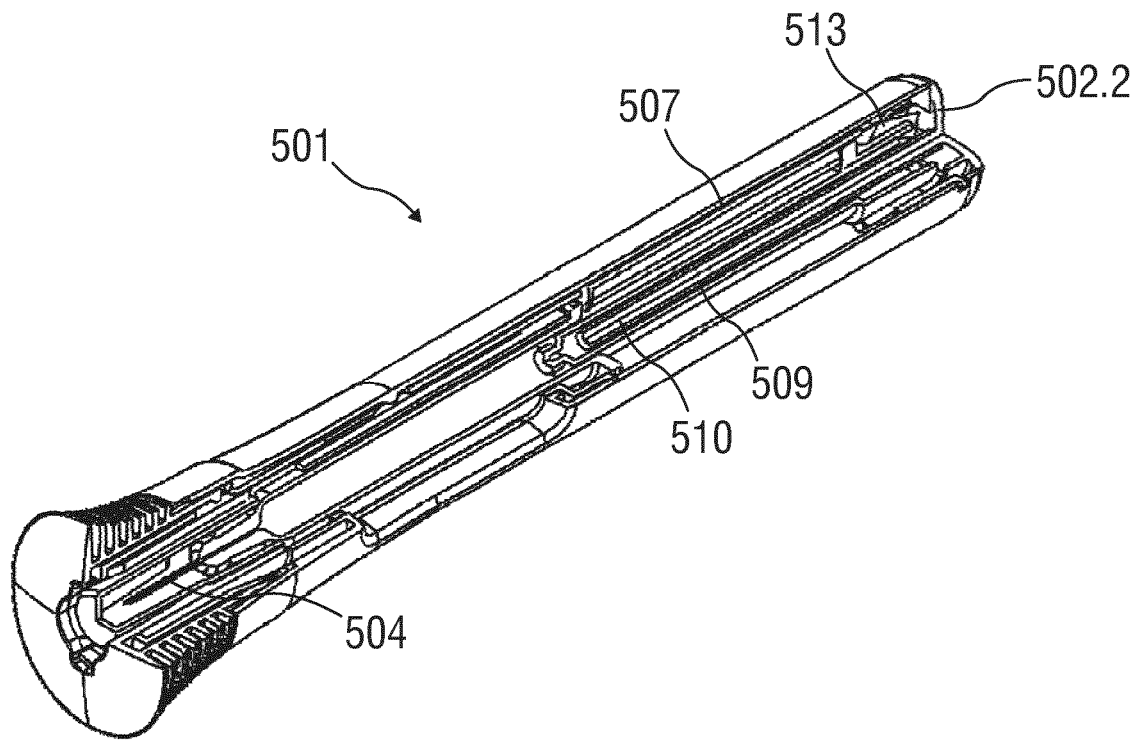
FIG. 31 is a schematic perspective partial section of a drug delivery device comprising an audible indicator according to a sixth embodiment.

FIG. 31 shows a schematic perspective partial section of an exemplary embodiment of a drug delivery device 501 comprising an audible indicator 513 according to the sixth embodiment.

The drug delivery device 501 is configured as an autoinjector similar to the one described in FIG. 1.

Except for the rear case 502.2 and the audible indicator 513, all components of the drug delivery device 1 substantially have the same configuration as described above in FIGS. 1 to 6. The audible indicator 513 according to the fifth embodiment will be described in more detail in FIG. 32. The rear case 502.2 will be described in more detail in FIG. 33.

Figure 32:
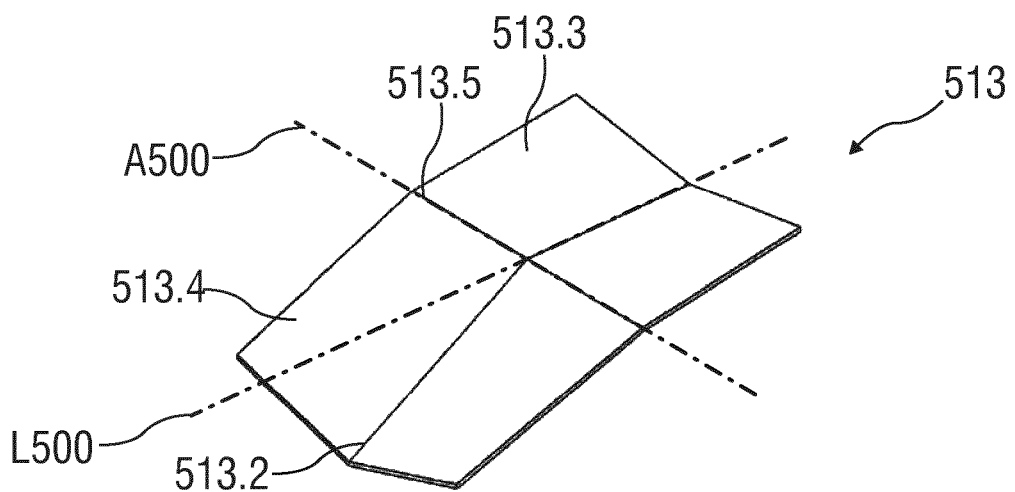
FIG. 32 is a schematic perspective view of the audible indicator according to the sixth embodiment in a pre-assembled state.

FIG. 32 is a perspective view of the audible indicator 513 according to the sixth embodiment.

The audible indicator 513 comprises a resilient force member 513.1 that is configured as a bistable leaf spring comprising a resilient material, e.g. spring steel or spring plastic. Thus, the resilient force member 513.1 is capable of residing in two states. That is, the resilient force member 513.1 may assume two different stable conformations with limited or no application of an external force. For example, these two states can include a first or relaxed state S1 (or pre-assembly state, or trigged state), in which the resilient force member 513.1 has a first conformation. In a second or biased state S2 (or primed state), the resilient force member 513.1 can have a second conformation. The resilient force member 513.1 may comprise a substantially rectangular shape and a longitudinal axis L500 running in parallel to the longest side of the outer circumference of the resilient force member 513.1.

The resilient force member 513.1 further comprises a longitudinal bend 513.2 that can be arranged generally in the enter of the resilient force member 513.1 running in parallel to the longitudinal axis L500. The longitudinal bend 513.2 divides the resilient force member 513.1 into two wing-shaped sections angled to each other with an angle less than 180 degrees.

The resilient force member 513.1 can be further divided into a proximal spring section 513.3 and a distal spring section 513.4 due to a cross bend 513.5 that extends in parallel to an axis A500 that may be perpendicular to the longitudinal axis L500.

According to FIG. 32, the resilient force member 513.1 is in the biased state S2, wherein the distal spring section 513.5 is bent about a certain angle over the cross bend 513.5 with respect to the proximal spring section 513.3.

With respect to the longitudinal axis L500 the resilient force member 513.1 of the present embodiment is smaller than the resilient force member 513.1 of the audible indicator 413 of the fifth embodiment.

Figure 33:
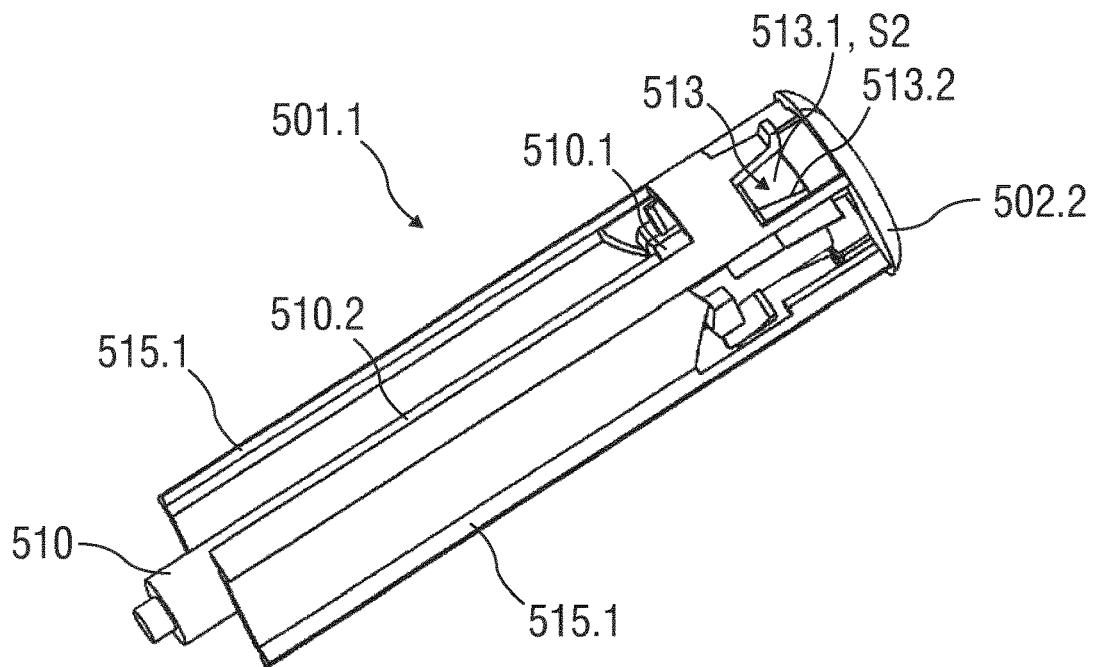
FIG. 33 is a schematic perspective view of a drive sub assembly of the drug delivery device comprising a rear case, a plunger and the audible indicator according to the sixth embodiment.

The resilient force member 513.1 is coupled to the rear case 502.2 as illustrated in FIG. 33.

FIG. 33 shows a schematic perspective view of a drive sub assembly 501.1 of the drug delivery device 501 comprising the rear case 502.2, a plunger 510, and the audible indicator 513 according to the sixth embodiment.

The rear case 502.2 comprises two support arms 515.1 similar to the ones described in FIG. 4.

According to the present embodiment, the support arms 515.1 have the same length with respect to the longitudinal axis L500 in an assembled state of the audible indicator 513.

The resilient force member 513.1 is coupled to the plunger 510, wherein the distal spring section 513.4 is fixed to a proximal plunger section 510.1 by a force fit, form fit and/or adhesive bond in order to prevent a rotational movement of the resilient force member 513.1 with respect to the plunger 510. The proximal spring section 513.3 defines a free end of the resilient force member 513.1 that protrudes beyond the edge of the proximal plunger section 510.1 as illustrated in FIG. 34.

The proximal spring section 513.3 is angled radially inwards with respect to the distal spring section 513.4; hence the resilient force member 513.1 is in the biased state S2, thereby storing energy.

Figure 34:
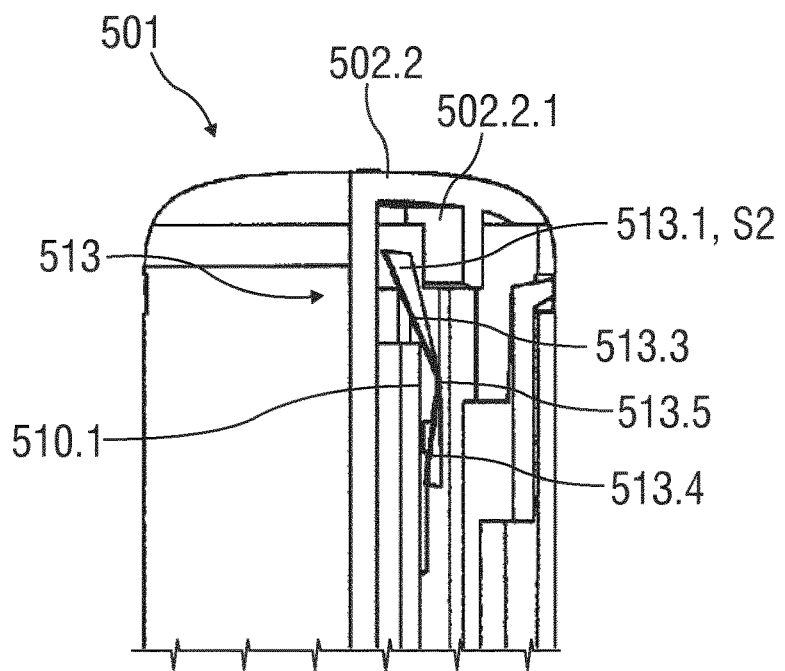
FIG. 34 is a schematic longitudinal section of a proximal part of a drug delivery device in a primed state comprising the audible indicator according to the sixth embodiment in a biased state.

The resilient force member 513.1, in particular the proximal spring section 513.3, is supported by the rear case 502.2 as illustrated and described in more detail in FIG. 34.

FIG. 34 shows a schematic longitudinal section of a proximal part of the drug delivery device 501 comprising the audible indicator 513 according to the sixth embodiment.

The drug delivery device 501 is in a primed state prior to use, wherein the plunger 510 is in a proximal position.

The proximal spring section 513.3 is supported by a supporting protrusion 502.2.1 arranged on an inner side of a proximal end of the rear case 502.2 projecting distally towards the plunger 510. The supporting protrusion 502.2.1 may be configured as a protruding section or as a circulated ring-shaped protrusion.

The proximal spring section 513.3 is arranged behind the supporting protrusion 502.2.1 with respect to a radial inward direction and is thus prevented against deflecting radially outwards during storage, transportation and priming of the drug delivery device 501. Furthermore, the cross bend 513.5 defines a kink enabling the bistability of the resilient force member 513.1.

Figure 35:
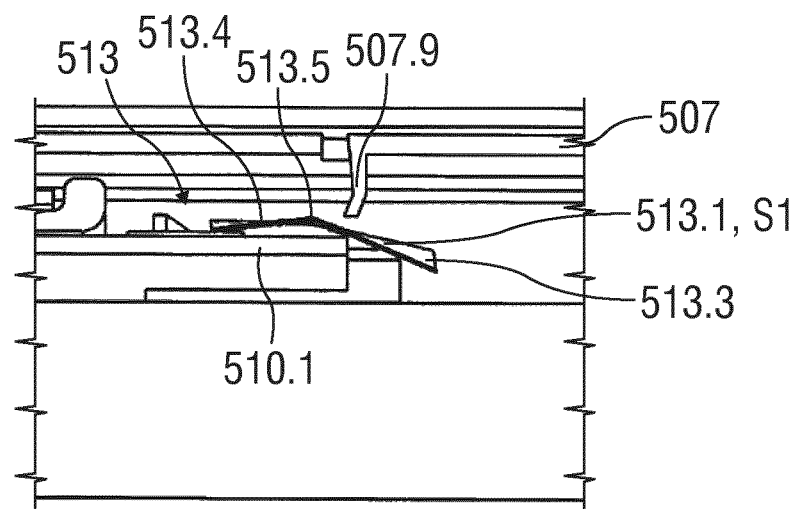
FIG. 35 is a schematic longitudinal section of the proximal part of the drug delivery device with the audible indicator according to FIG. 34 in a relaxed state.

For delivering a medicament M through a needle 504 into an injection site, the plunger 510 has to be moved distally from the proximal position to the distal position as illustrated in FIG. 35 due to the activation of a drive spring 509 as described above. Because the distal spring section 513.4 is fixed to the proximal plunger section 510.1, the resilient force member 513.1 follows the axial movement of the plunger 510. As a consequence, the resilient force member 513.1 moves distally with respect to the rear case 502.2 away from the supporting protrusion 502.2.1, wherein the proximal spring section 513.3 becomes unsupported.

At the end of medicament delivery, an activating rib 507.9 arranged on an inner circumference of a needle shroud 507 abuts the resilient force member 513.1 at the cross bend 513.5. This abutting generates a force influence on the resilient force member 513.1, which stimulates the proximal spring section 413.5 to deflect radially outwards.

Due to the deflection of the proximal spring section 513.5, the energy is released from the resilient force member 513.1. By releasing the stored energy, the resilient force member 513.1 can transition from a generally biased state S2 into a generally relaxed state S1 as illustrated in FIG. 35, thereby generating a recognizable audible signal.

FIG. 35 shows a schematic longitudinal section of the proximal part of the drug delivery device 501, wherein the audible indicator 513 is in the biased state S2, but on the point of activation as it is starting to contact the needle shroud 507.

FIGS. 36 to 40 respectively show an audible indicator 613 according to a seventh embodiment.

Figure 36:
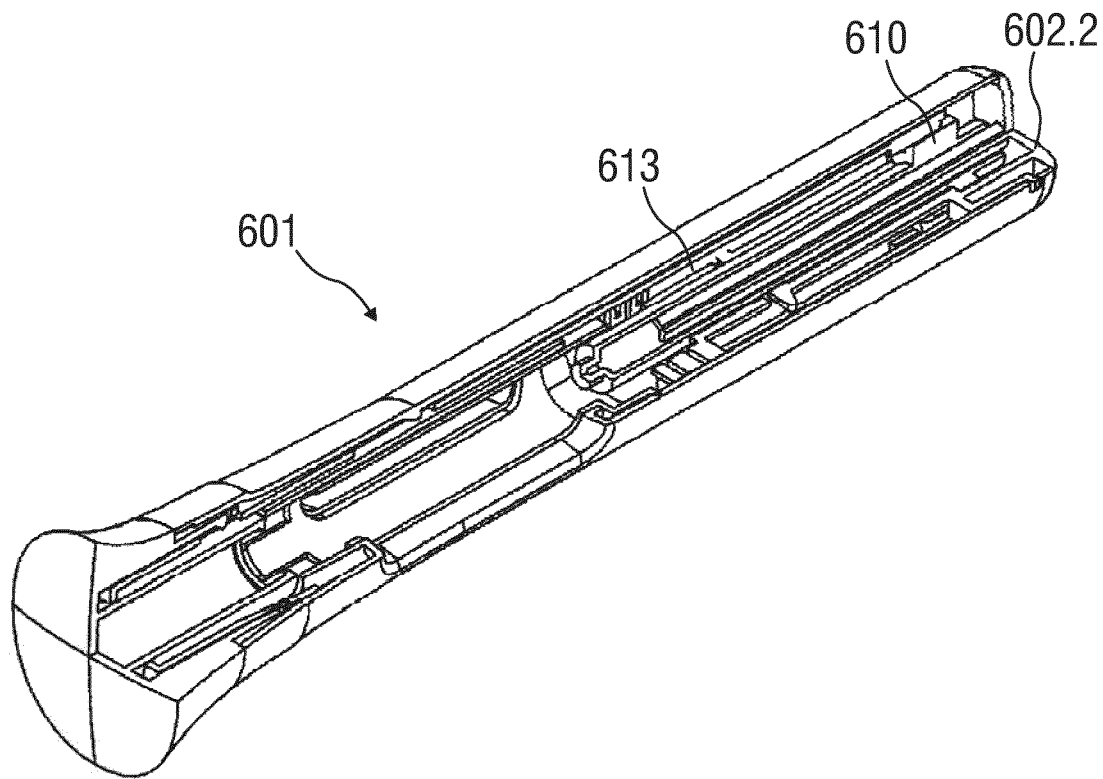
FIG. 36 is a schematic perspective partial section of a drug delivery device comprising an audible indicator according to a seventh embodiment.

FIG. 36 shows a schematic perspective partial section of an exemplary embodiment of a drug delivery device 601 comprising an audible indicator 613 according to a seventh embodiment.

The drug delivery device 601 is configured as an autoinjector similar to the one described in FIG. 1.

Except for the rear case 602.2 and the audible indicator 613, all components of the drug delivery device 601 substantially have the same configuration as described above in the FIGS. 1 to 6. The audible indicator 613 according to the seventh embodiment will be described in more detail in FIG. 32. The rear case 602.2 will be described in more detail in FIG. 37.

Figure 37:
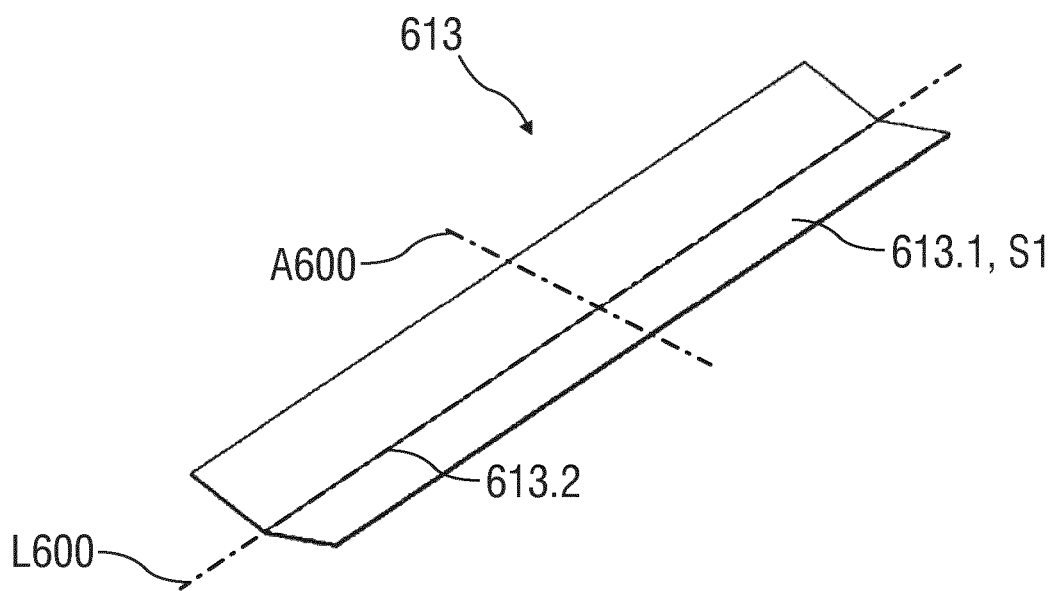
FIG. 37 is a schematic perspective view of the audible indicator according to the seventh embodiment in a pre-assembled state.

FIG. 37 is a perspective view of the audible indicator 613 according to the seventh embodiment.

The audible indicator 613 comprises a resilient force member 613.1 that is configured as a monostable leaf spring comprising a resilient material, e.g. spring steel or spring plastic. Thus, the resilient force member 613.1 is capable of residing in two states. That is, the resilient force member 613.1 may assume two different conformations, one of them stable with limited or no application of an external force and the other one unstable. For example, these two states can include a first or relaxed state S1 (or pre-assembly state, or trigged state), in which the resilient force member 613.1 has a first conformation. In a second or biased state S2 (or primed state), the resilient force member 613.1 can have a second conformation. The resilient force member 613.1 may comprise a substantially rectangular shape and a longitudinal axis L600 running in parallel to the longest side of the outer circumference of the resilient force member 613.1.

The resilient force member 613.1 further comprises a longitudinal bend 613.2 that may be arranged generally in the center of the resilient force member 613.1 running in parallel to the longitudinal axis L600. The longitudinal bend 613.2 divides the resilient force member 613.1 into two wing-shaped sections angled to each other with an angle less than 180 degrees.

Figure 38:
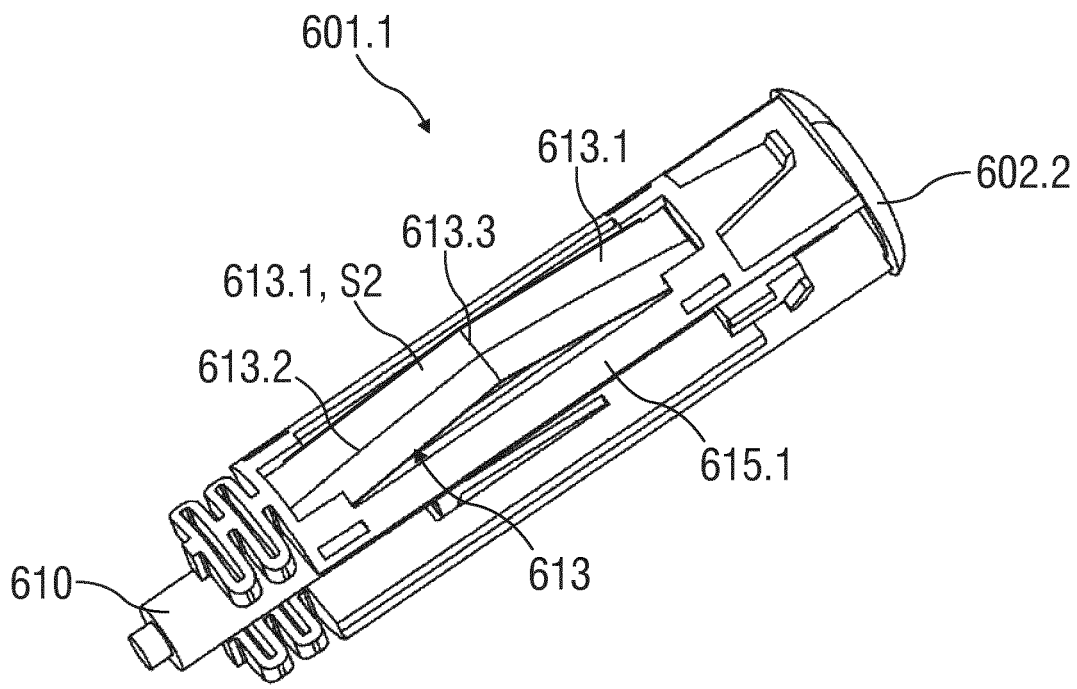
FIG. 38 is a schematic perspective view of a drive sub assembly of the drug delivery device comprising a rear case, a plunger and the audible indicator according to the seventh embodiment.

The resilient force member 613.1 is coupled to the rear case 602.2 as illustrated in FIG. 38.

FIG. 38 shows a schematic perspective view of a drive sub assembly 601.1 of the drug delivery device 601 comprising the rear case 602.2, a plunger 610, and the audible indicator 613 according to the seventh embodiment.

The rear case 602.2 comprises two support arms 615.1 similar to the ones described in FIG. 14.

According to the present embodiment, the support arms 615.1 have the same length with respect to the longitudinal axis L600 in an assembled state of the audible indicator 613. The support arms 615.1 respectively comprise a longitudinal recess 615.1.1, wherein the resilient force member 613.1 is arranged within the longitudinal recess 615.1.1 of one of the support arms 615.1. Thereby, the resilient force member 613.1 is proximally and distally fixed to the support arm 615.1 by a positive connection, e.g. a snap connection, in order to prevent a rotation of the resilient force member 613.1. Alternatively, the fixing could allow rotation of the ends of the resilient force member 613.1, but prevent translational movement.

The wing-shaped sections of the resilient force member 613.1 are bent upwards away from the plunger 610.

According to the present embodiment, the audible indicator 613 comprises only a monostability in contrast to the bistable resilient force members 113.1 to 513.1 of some of the other embodiments. That means, the resilient force member 613.1 needs to be supported for remaining in a biased state S2 as illustrated and described in more detail in FIG. 39.

Figure 39:
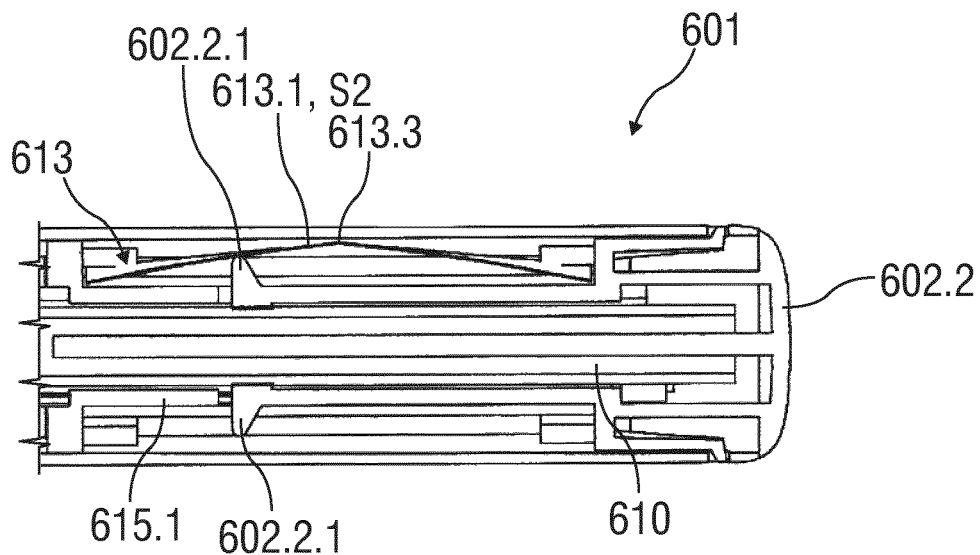
FIG. 39 is a schematic longitudinal section of a proximal part of a drug delivery device in a primed state comprising the audible indicator according to the seventh embodiment in a biased state.

FIG. 39 shows a schematic longitudinal section of a proximal part of the drug delivery device 601, wherein the resilient force member 613.1 is in the biased state S2 and the drug delivery device 601 is in a primed state prior to use, wherein the plunger 610 is in a proximal position.

The support of the resilient force member 613.1 is achieved by a cantilever beam 602.2.1 arranged on a section of the support arm 615.1 behind the resilient force member 613.1 with respect to a radial inward direction. Thus, the resilient force member 613.1 rests on the cantilever beam 602.2.1, whereby the resilient force member 613.1 is additionally bent in the center about an axis A600 that runs generally perpendicular to the longitudinal axis L600, thereby generating a kink tip 613.3.

The cantilever beam 602.2.1 is biased radially outwards by an outer circumference of the plunger 610. According to the present embodiment, the rear case 602.2 comprises two cantilever beams 602.2.1. Alternatively, the rear case 602.2 may comprise only one or more than two cantilever beams 602.2.1. In embodiments with more than one resilient force member 613.1, each cantilever beam 602.2.1 may be arranged to support one respective resilient force member 613.1.

Figure 40:
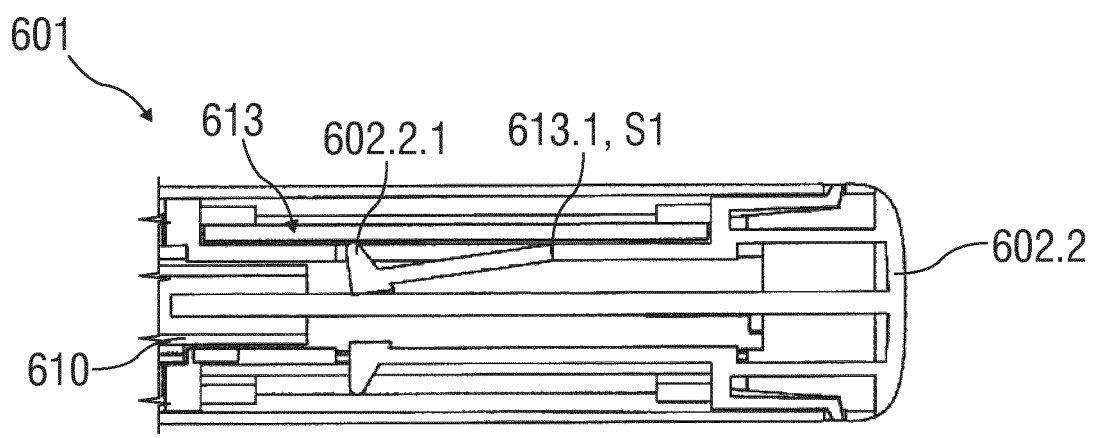
FIG. 40 is a schematic longitudinal section of the proximal part of the drug delivery device with the audible indicator according to the seventh embodiment in a relaxed state.

For delivering a medicament M into an injection site, the plunger 610 has to be moved distally from the proximal position to the distal position as illustrated in FIG. 40. During medicament delivery, the resilient force member 613.1 is supported by the cantilever beam 602.2.1. During movement of the plunger 610, a friction is induced on the cantilever beam 602.2.1.

At the end of medicament delivery, when a proximal end of the plunger 610 passes the cantilever beam 602.2.1 distally, the cantilever beam 602.2.1 is free to relax radially inwards. As a consequence, the resilient force element 613.1 relaxes, thereby generating a recognizable audible signal.

FIG. 40 shows a schematic longitudinal section of the proximal part of the drug delivery device 601, wherein the resilient force element 613 is in the relaxed state S1 after medicament delivery.

The skilled person readily understands that application of the audible indicator 13 is not limited to auto-injectors 1. Instead, the audible indicator 13 may likewise be applied in a manually operated drug delivery device 1 for indicating that the plunger 10 has been completely moved into the distal position.

In an exemplary embodiment, the bistable or monostable resilient force member 13.1, 113.1, 213.1, 313.1, 413.1, 513.1, 613.1 may consist of stainless steel, e.g. stainless steel 301 full hard. In an exemplary embodiment the resilient force member 13.1, 113.1, 213.1, 313.1, 413.1, 513.1, 613.1 may have a substantially rectangular form, in particular with a length of 70 mm. A nominal width flat of the resilient force member 13.1, 113.1, 213.1, 313.1, 413.1, 513.1, 613.1 may be approximately 8 mm. The longitudinal bend 13.2, 113.2, 213.2, 313.2, 413.2, 513.2, 613.2 may be positioned to bisect the width of the resilient force member 13.1, 113.1, 213.1, 313.1, 413.1, 513.1, 613.1. A thickness of the resilient force member 13.1, 113.1, 213.1, 313.1, 413.1, 513.1, 613.1 may be 0.1 mm. In the first conformation, the resilient force member 13.1, 113.1, 213.1, 313.1, 413.1, 513.1, 613.1 may be bent about the longitudinal bend 13.2, 113.2, 213.2, 313.2, 413.2, 513.2, 613.2 such that the two-wing-shaped sections are at an angle of between 130 and 160 degrees or between 130 degrees and 150 degrees. For example, the angle can be between 130 degrees and 140 degrees or between 140 degrees and 155 degrees or between 132 degrees and 142 degrees or between 134 degrees and 140 degrees or between 136 degrees and 138 degrees. In an exemplary embodiment the angle is approximately or exactly 136 degrees or 137 degrees or 138 degrees or 148 degrees or 152 degrees relative to each other.

In other exemplary embodiments, the resilient force member 13.1, 113.1, 213.1, 313.1, 413.1, 513.1, 613.1 may have a different length, e.g. approximately 30 mm or 43 mm.

In order to kink the resilient force member 13.1, 113.1, 213.1, 313.1, 413.1, 513.1, 613.1 to move it from the first conformation to the second conformation a force in the range from 3 N to 14 N may be applied to a free end of the resilient force member 13.1, 113.1, 213.1, 313.1, 413.1, 513.1, 613.1 or to a point near the free end, e.g. approximately 13 mm from the free end. Application of this force may result in an extension of 2 mm to 3.5 mm of the free end from its position in the first conformation.

A force required to activate the resilient force member 13.1, 113.1, 213.1, 313.1, 413.1, 513.1, 613.1 to move it from its second conformation to its first conformation may be in a range from 0.2 N to 0.4 N applied to the free end of the resilient force member 13.1, 113.1, 213.1, 313.1, 413.1, 513.1, 613.1 or to a point near the free end, e.g. approximately 1 mm to 2 mm from the free end.

A particularly clear click noise and reduced kinking and activation forces may be achieved by kinking the resilient force member 13.1, 113.1, 213.1, 313.1, 413.1, 513.1, 613.1, activating it and then kinking it again before inserting it into the drug delivery device 1, 101, 201, 301, 401, 501, 601.

When activated, the resilient force member 13.1, 113.1, 213.1, 313.1, 413.1, 513.1, 613.1 may produce an audible signal with a volume of at least 100 dB, e.g. measured at a distance of approximately 0.5 m. As opposed to a resilient force member 13.1, 113.1, 213.1, 313.1, 413.1, 513.1, 613.1 with a bend angle of e.g. 152 degrees, the volume produced by a resilient force member 13.1, 113.1, 213.1, 313.1, 413.1, 513.1, 613.1 having a bend angle of e.g. 136 degrees can be increased by approximately 6 dB, which corresponds to a factor 2 increase in amplitude.

When inserted in a drug delivery device 1, 101, 201, 301, 401, 501, 601, the resilient force member 13.1, 113.1, 213.1, 313.1, 413.1, 513.1, 613.1 may produce an audible signal with a volume of at least 100 dB(A), e.g. measured at a distance of approximately 150 mm. In a test setup, the drug delivery device 1, 101, 201, 301, 401, 501, 601 was placed in a sound-absorbing environment on a table with the needle shroud 7, 307, 407, 507 ahead. An elastomeric layer was located between the needle shroud 7, 307, 407, 507 and the table to acoustically decouple the drug delivery device 1, 101, 201, 301, 401, 501, 601 from the table. Two microphones (e.g. ROGA MI-17 (IEPE)) were placed laterally from the drug delivery device 1, 101, 201, 301, 401, 501, 601 opposite each other at a distance of 150 mm, respectively and 170 mm above the table. A first test was performed with a user holding and operating the drug delivery device 1, 101, 201, 301, 401, 501, 601 with the right hand closed around the drug delivery device 1, 101, 201, 301, 401, 501, 601, wherein the fingers of the hand covered one side of the drug delivery device 1, 101, 201, 301, 401, 501, 601 directed towards one of the microphones and wherein the opposite side pointing towards the other microphone was covered by the palm of the hand. The volume of the audible signal on the finger side microphone was at least 100 dB(A) while the volume on the palm side microphone was lower than 100 dB(A). Another test was performed with a user holding and operating the drug delivery device 1, 101, 201, 301, 401, 501, 601 only with the fingertips of the right hand, wherein the palm of the hand was located between the drug delivery device 1, 101, 201, 301, 401, 501, 601 and one of the microphones; however, the drug delivery device 1, 101, 201, 301, 401, 501, 601 was not touched by the palm. The volume of the audible signal acquired by both microphones was at least 100 dB(A), wherein the volume detected by the palm side microphone was slightly lower than the volume detected by the other microphone.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 1, 101, 201, 301, 401, 501, 601 drug delivery device
1.1, 101.1, 201.1, 301.1, 401.1, 501.1, 601.1 drive sub assembly
2 case
2.1 front case
2.2, 102.1, 202.1, 302.1, 402.1, 502.1, 602.2 rear case
502.2.1 supporting protrusion
602.2.1 cantilever beam
2.15 radial stop
3 medicament container, syringe
4, 104, 404, 504 needle
5 protective needle sheath
6 stopper
7, 307, 407, 507 needle shroud 7.6 apertures
307.7 supporting rib
407.8 locking rib
507.9 activation rib
8 shroud spring
9, 109, 409, 509 drive spring
10, 110, 210, 310, 410, 510, 610 plunger
10.1, 110.1, 210.1, 310.1, 410.1, 510.1 proximal plunger section
10.2, 110.2, 210.2, 310.2, 410.1, 510.2 distal plunger section
11 cap
11.1 grip features
11.2 grip element
11.3 compliant beams
11.4 rib
12 plunger release mechanism
13, 113, 213, 313, 413, 513, 613 audible indicator
13.1, 113.1, 213.1, 313.1, 413.1, 513.1, 613.1 resilient force member
13.1.1 distally pointing end
13.1.2 proximally pointing end
13.2, 113.2, 213.2, 313.2, 413.2, 513.2, 613.2 longitudinal bend
13.3 tabs
113.3 proximal spring section
113.4 distal spring section
113.5 cross bend
213.3 kink tip
313.3, 413.4, 513.3 proximal spring section
313.4, 413.4 intermediate spring section
313.5, 413.5 distal spring section
313.5.1 hook-like projection
313.6, 413.6 first cross bend
313.7, 413.7 second cross bend
513.4 distal spring section
513.5 cross bend
613.3 kink tip
14 shroud lock mechanism
15.1, 115.1, 215.1, 315.1, 415.1, 515.1, 615.1 support arms
215.1.1 longitudinal recess
315.1.1 guiding recess
315.1.2, 415.2.1 locking tabs
415.2 fixing element
615.1.1 longitudinal recess
15.2 flexible arm
15.2.1 projection
16 carrier
418 collar
418.1 collar ramp
A, A100, A200, A300, A400, A500, A600 axis
C force-bending curve
L, L100, L200, L300, L400, L500, L600 longitudinal axis
M medicament
S1 relaxed state
S2 biased state
x abscissa
y ordinate
x1, y2 coordinates
x2, y1 coordinates

The invention claimed is:

1. An audible indicator for use with a drug delivery device, the audible indicator comprising: a monostatic resilient force member configured to reside in two or more states having two or more different conformations, wherein in a relaxed state, the monostable resilient force member is relaxed in a first conformation, wherein in a biased state, the monostable resilient force member is biased to store energy in a second conformation different from the first conformation and configured to remain in the second conformation while a first force is maintained, the first force being lower than a force needed for changing from the relaxed state to the biased state, and wherein the monostable resilient force member releases the stored energy to generate an audible signal when changing from the biased state into the relaxed state due to a transition from the second conformation to the first conformation, wherein the monostable resilient force member is supported by a retaining element in the biased state in order to prevent the transition into the relaxed state.

2. The audible indicator according to claim 1, wherein the monostable resilient force member is configured to be supported when the drug delivery device is in an initial state.

3. The audible indicator according to claim 1, wherein the monostable resilient force member is configured to supported when the drug delivery device is in an initial state and in a primed state, and wherein a proximal spring section of the monostable resilient force member is configured to be supported by a supporting protrusion arranged on a rear case.

4. The audible indicator according to claim 1, configured to produce an audible signal with a sound intensity of at least 100 dB.

5. The audible indicator according to claim 1, wherein the retaining element comprises a plunger, wherein the monostable resilient force member is allowed to transition from the biased state by a movement of the plunger.

6. The audible indicator according to claim 5, wherein the monostable resilient force member is allowed to transition from the biased state into the relaxed state by the movement of the plunger towards a distal position at an end of a medicament delivery process by the drug delivery device.

7. The audible indicator according to claim 1, wherein the monostable resilient force member includes a leaf spring defining a longitudinal axis, and wherein the monostable resilient force member is configured to be bent by a certain angle about the longitudinal axis to form two angled wing-shaped sections.

8. The audible indicator according to claim 7, wherein the leaf spring has a rectangular shape, a square shape, or an oval shape.

9. The audible indicator according to claim 7, wherein the monostable resilient force member is bent about the longitudinal axis such that the two-wing-shaped sections are at an angle of between 130 degrees and 160 degrees relative to each other.

10. The audible indicator according to claim 1, wherein the retaining element is adapted to be moved or allowed to move by a plunger or by a drive spring, wherein movement of the retaining element allows transition of the monostable resilient force member from the biased state.

11. The audible indicator according to claim 10, wherein the retaining element comprises a flexible arm arranged on a rear case, and wherein the monostable resilient force member rests in the biased state by support of the flexible arm.

12. The audible indicator according to claim 11, wherein the flexible arm is biased by an outer circumference of the plunger, wherein the monostable resilient force member is configured to transition from the biased state into the relaxed state when the flexible arm releases.

13. The audible indicator according to claim 10, wherein the retaining element comprises a cantilever beam arranged on a rear case, and wherein the monostable resilient force member is configured to rest in the biased state by support of the cantilever beam.

14. The audible indicator according to claim 13, wherein the cantilever beam is biased by an outer circumference of the plunges, and wherein the monostable resilient force member is configured to transition from the biased state into the relaxed state when the cantilever beam releases.

15. A drug delivery device, comprising: a retaining element; and an audible indicator comprising a monostable resilient force member configured to reside in two or more states having two or more different conformations, wherein in a relaxed state, the monostable resilient three member is relaxed in a first conformation, wherein in a biased state, the monostable resilient force member is biased to store energy in a second conformation different from the first conformation and configured to remain in the second conformation while a first force is maintained, the first force being lower than a force needed for changing from the relaxed state to the biased state, and wherein the monostable resilient force member releases the stored energy to generate an audible signal when changing from the biased state into the relaxed state due to a transition from the second conformation to the first conformation, wherein the monostable resilient force member is supported by the retaining element the biased state in order to prevent the transition into the relaxed state.

16. The drug delivery device of claim 15, comprising a medicament container containing a pharmaceutically active compound.

17. An audible indicator for use with a drug delivery device, the audible indicator comprising: a resilient force member configured to reside in two or more states having two or more different conformations, wherein in a relaxed state, the resilient force member is relaxed in a first conformation, wherein in a biased state, the resilient force member is biased to store energy in a second conformation different from the first conformation, wherein the resilient force member releases the stored energy to generate an audible signal when changing, from the biased state into the relaxed state due to a transition from the second conformation to the first conformation, wherein the resilient force member is supported by a retaining element in the biased state in order to prevent the transition into the relaxed state, wherein the resilient force member includes a leaf spring defining a longitudinal axis, and wherein the resilient force member is configured to be bent by a certain angle about the longitudinal axis to form two angled wing-shaped sections.

* * * * *

UNITED STATES PATENT AND TRADEMARK OFFICE
CERTIFICATE OF CORRECTION

PATENT NO. : 10,918,811 B2  
APPLICATION NO. : 15/578491  
DATED : February 16, 2021  
INVENTOR(S) : Carsten Mosebach et al.

Page 1 of 1

It is certified that error appears in the above-identified patent and that said Letters Patent is hereby corrected as shown below:

In the Claims

In Column 27, Line 64, Claim 1, delete "monostatic" and insert -- monostable --

In Column 28, Line 19, Claim 3, before "supported" insert -- be --

In Column 29, Line 6, Claim 14, delete "plunges," and insert -- plunger, --

In Column 29, Line 13 (approx.), Claim 15, delete "three" and insert -- force --

In Column 30, Line 1, Claim 15, after "element" insert -- in --

In Column 30, Line 15, Claim 17, delete "changing," and insert -- changing --

Signed and Sealed this  
Twenty-fourth Day of August, 2021

Drew Hirshfeld  
*Performing the Functions and Duties of the*  
*Under Secretary of Commerce for Intellectual Property and*  
*Director of the United States Patent and Trademark Office*